(12) United States Patent
Kang et al.

(10) Patent No.: US 11,298,108 B2
(45) Date of Patent: Apr. 12, 2022

(54) ULTRASOUND MEDICAL IMAGING APPARATUS AND METHOD OF CONTROLLING THE SAME

(71) Applicant: SAMSUNG MEDISON CO., LTD., Hongcheon-gun (KR)

(72) Inventors: Young-seok Kang, Suwon-si (KR); Dae-hwan Kim, Suwon-si (KR); Mi-ae Byun, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1015 days.

(21) Appl. No.: 15/871,200

(22) Filed: Jan. 15, 2018

(65) Prior Publication Data

US 2019/0200960 A1 Jul. 4, 2019

(30) Foreign Application Priority Data

Dec. 28, 2017 (KR) .......................... 10-2017-0182593

(51) Int. Cl.
*A61B 8/00* (2006.01)
*G16H 40/67* (2018.01)
(Continued)

(52) U.S. Cl.
CPC .............. *A61B 8/461* (2013.01); *A61B 8/06* (2013.01); *A61B 8/14* (2013.01); *A61B 8/4427* (2013.01);
(Continued)

(58) Field of Classification Search
CPC .................................................... A61B 8/461
See application file for complete search history.

(56) References Cited

U.S. PATENT DOCUMENTS

| 5,718,228 A | 2/1998 | Hiruta et al. |
| 9,218,452 B2 | 12/2015 | Varna et al. |
| 9,525,886 B2 | 12/2016 | Lee |
| 2006/0036147 A1 | 2/2006 | Sathyanarayana |

(Continued)

FOREIGN PATENT DOCUMENTS

| JP | 6-325141 A | 11/1994 |
| JP | 11-347033 A | 12/1999 |

(Continued)

OTHER PUBLICATIONS

Communication dated Nov. 19, 2018, issued by the European Patent Office in counterpart European Application No. 18162536.9.

*Primary Examiner* — Joseph M Santos Rodriguez
(74) *Attorney, Agent, or Firm* — Sughrue Mion, PLLC

(57) ABSTRACT

Provided are an ultrasound medical imaging apparatus and a method of controlling the ultrasound medical imaging apparatus. The ultrasound medical imaging apparatus includes: an ultrasound probe configured to transmit an ultrasound signal to an object and receive an ultrasound echo signal from the object; at least one processor configured to obtain ultrasound image data by using the ultrasound echo signal and generate ultrasound streaming image data of the object based on the ultrasound image data; and a communicator configured to transmit the ultrasound streaming image data to an external device, wherein the at least one processor is further configured to generate ultrasound still image data based on the ultrasound image data when a preset event occurs, and the communicator is further configured to transmit the ultrasound still image data to the external device.

18 Claims, 15 Drawing Sheets
(2 of 15 Drawing Sheet(s) Filed in Color)

(51) Int. Cl.
  *G16H 30/20* (2018.01)
  *G06F 3/14* (2006.01)
  *G09G 5/14* (2006.01)
  *G16H 40/63* (2018.01)
  *G16H 15/00* (2018.01)
  *A61B 8/06* (2006.01)
  *A61B 8/14* (2006.01)
  *A61B 8/08* (2006.01)
  *G01S 7/52* (2006.01)

(52) U.S. Cl.
  CPC .............. *A61B 8/467* (2013.01); *A61B 8/483* (2013.01); *A61B 8/54* (2013.01); *A61B 8/565* (2013.01); *G06F 3/1462* (2013.01); *G09G 5/14* (2013.01); *G16H 15/00* (2018.01); *G16H 30/20* (2018.01); *G16H 40/63* (2018.01); *G16H 40/67* (2018.01); *A61B 8/0866* (2013.01); *A61B 8/4405* (2013.01); *A61B 8/463* (2013.01); *G01S 7/52074* (2013.01); *G06F 3/14* (2013.01); *G09G 2340/02* (2013.01); *G09G 2340/0407* (2013.01); *G09G 2370/16* (2013.01)

(56) References Cited

U.S. PATENT DOCUMENTS

| | | |
|---|---|---|
| 2006/0173318 A1 | 8/2006 | Sathyanarayan |
| 2016/0066893 A1 | 3/2016 | Cho et al. |
| 2016/0100824 A1 | 4/2016 | Kim |
| 2016/0173770 A1 | 6/2016 | Fosodeder et al. |
| 2016/0338672 A1 | 11/2016 | Kanayama et al. |
| 2017/0011515 A1 | 1/2017 | Liu et al. |
| 2017/0031543 A1* | 2/2017 | Numakami ............... G09G 5/14 |
| 2017/0086798 A1 | 3/2017 | Bjaerum et al. |
| 2017/0105701 A1 | 4/2017 | Pelissier et al. |
| 2017/0105706 A1 | 4/2017 | Berger et al. |
| 2019/0336101 A1* | 11/2019 | Chiang ................. G01S 7/5202 |

FOREIGN PATENT DOCUMENTS

| | | |
|---|---|---|
| JP | 2001178718 A | 7/2001 |
| JP | 2005-58575 A | 3/2005 |
| JP | 4794631 B2 | 10/2011 |
| JP | 2012139491 A | 7/2012 |
| JP | 201554056 A | 3/2015 |
| JP | 2015-167777 A | 9/2015 |
| KR | 1020100036422 A | 4/2010 |
| KR | 101518291 B1 | 5/2015 |
| WO | 2014035175 A1 | 3/2014 |
| WO | 2017/064994 A1 | 4/2017 |

\* cited by examiner

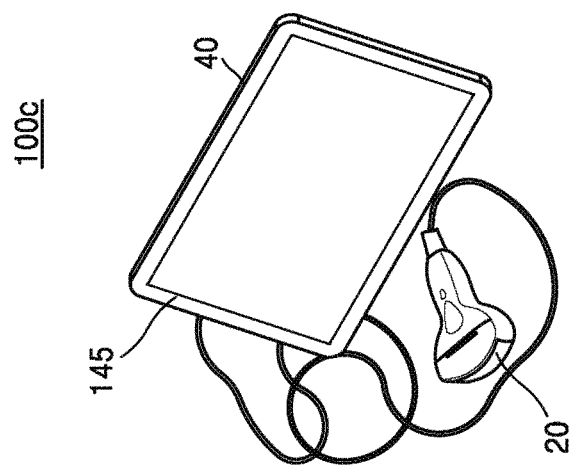
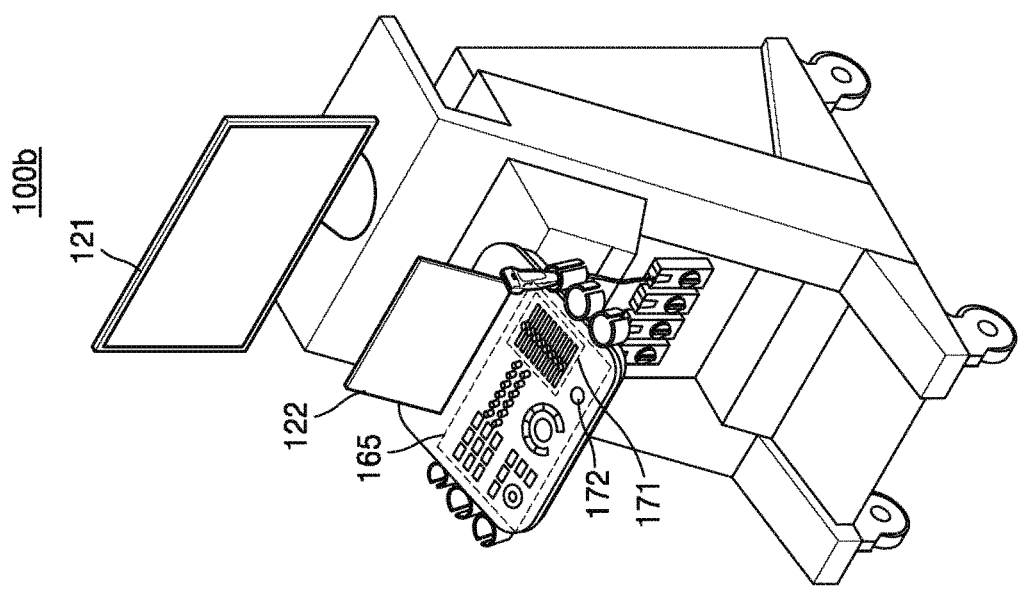
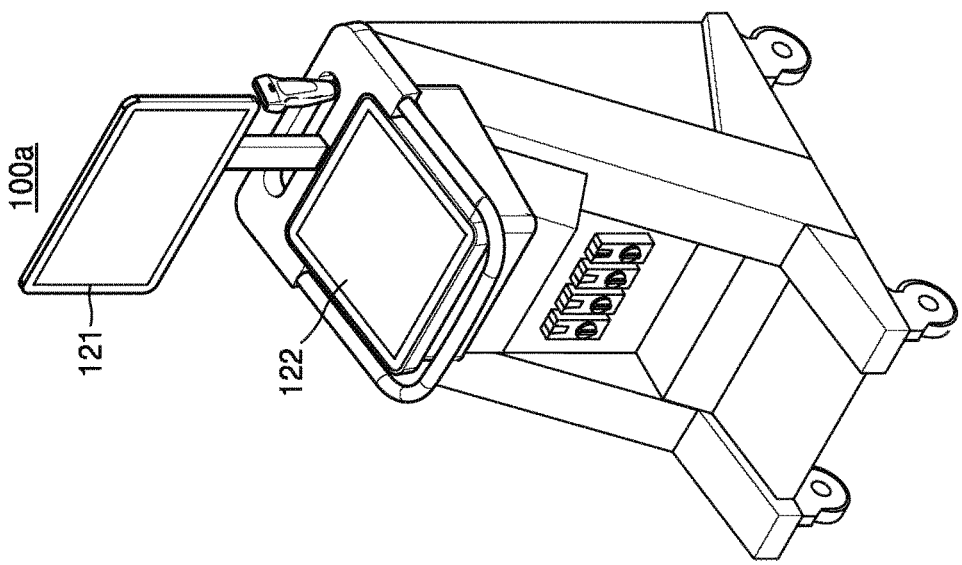

ULTRASOUND MEDICAL IMAGING APPARATUS AND METHOD OF CONTROLLING THE SAME

CROSS-REFERENCE TO RELATED APPLICATION(S)

This application is based on and claims priority under 35 U.S.C. § 119 to Korean Patent Application No. 10-2017-0182593, filed on Dec. 28, 2017, in the Korean Intellectual Property Office, the disclosure of which is incorporated by reference herein in its entirety.

BACKGROUND

1. Field

The present disclosure relates to ultrasound medical imaging apparatuses and methods of controlling the ultrasound medical imaging apparatuses.

2. Description of Related Art

Ultrasound diagnostic apparatuses transmit ultrasound signals generated by transducers of a probe to an object and detect information about signals reflected from the object, thereby obtaining at least one image of an internal part, for example, soft tissue or blood flow, of the object.

Ultrasound medical imaging apparatuses are small in size, cheap, and capable of displaying images in real-time. Also, ultrasound medical imaging apparatuses have excellent stability because there is no exposure to radiation, and thus, are being widely used with other imaging diagnosis apparatuses such as an X-ray diagnosis apparatus, a computerized tomography (CT) scanner, a magnetic resonance image (MRI) apparatus, a nuclear medicine diagnosis apparatus, etc.

Also, due to developments in a communication technology, remote treatment has become possible. For example, ultrasound images generated by an ultrasound medical imaging apparatus may be transferred to an external device in real-time, and then, a doctor may perform remote treatment while watching the ultrasound images in real-time even out of a hospital.

However, according to a communication state between an image transmitter and a receiver, there may be stuttering when streaming images. In order to address this stuttering of the streaming images, a method of transmitting/receiving streaming images by using an adaptive streaming mechanism technology has been suggested. The adaptive streaming mechanism technology involves optimizing a bit rate of a streaming image by analyzing a network environment between an image transmitter and a receiver.

However, when the streaming image is transferred by using the adaptive streaming mechanism technology, image quality degrades according to the network environment between the image transmitter and the receiver, and accordingly, it may be difficult for a doctor to perform remote treatment by using the streaming image.

SUMMARY

Provided are ultrasound medical imaging apparatuses capable of obtaining ultrasound still image data when a preset event occurs.

Provided are ultrasound medical imaging apparatuses capable of transferring high-quality ultrasound still image data when transmitting ultrasound streaming images.

Additional aspects will be set forth in part in the description which follows and, in part, will be apparent from the description, or may be learned by practice of the presented embodiments.

In accordance with an aspect of the present disclosure, an ultrasound medical imaging apparatus includes: an ultrasound probe configured to transmit an ultrasound signal to an object and receive an ultrasound echo signal from the object; at least one processor configured to obtain ultrasound image data by using the ultrasound echo signal and generate ultrasound streaming image data of the object based on the ultrasound image data; and a communicator configured to transmit the ultrasound streaming image data to an external device, wherein the at least one processor is further configured to generate ultrasound still image data based on the ultrasound image data when a preset event occurs, and the communicator is further configured to transmit the ultrasound still image data to the external device.

In accordance with another aspect of the present disclosure, a method of controlling an ultrasound medical imaging apparatus, the method includes: transmitting an ultrasound signal to an object and receiving an ultrasound echo signal from the object; obtaining ultrasound image data by using the ultrasound echo signal; generating ultrasound streaming image data of the object based on the ultrasound image data; transmitting the ultrasound streaming image data to an external device; when a preset event occurs, generating ultrasound still image data based on the ultrasound image data; and transmitting the ultrasound still image data to the external device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of embodiments, taken in conjunction with the accompanying drawings in which:

FIGS. 2A, 2B, and 2C are diagrams respectively illustrating an ultrasound diagnosis apparatus according to an embodiment;

DETAILED DESCRIPTION

Figure 1:
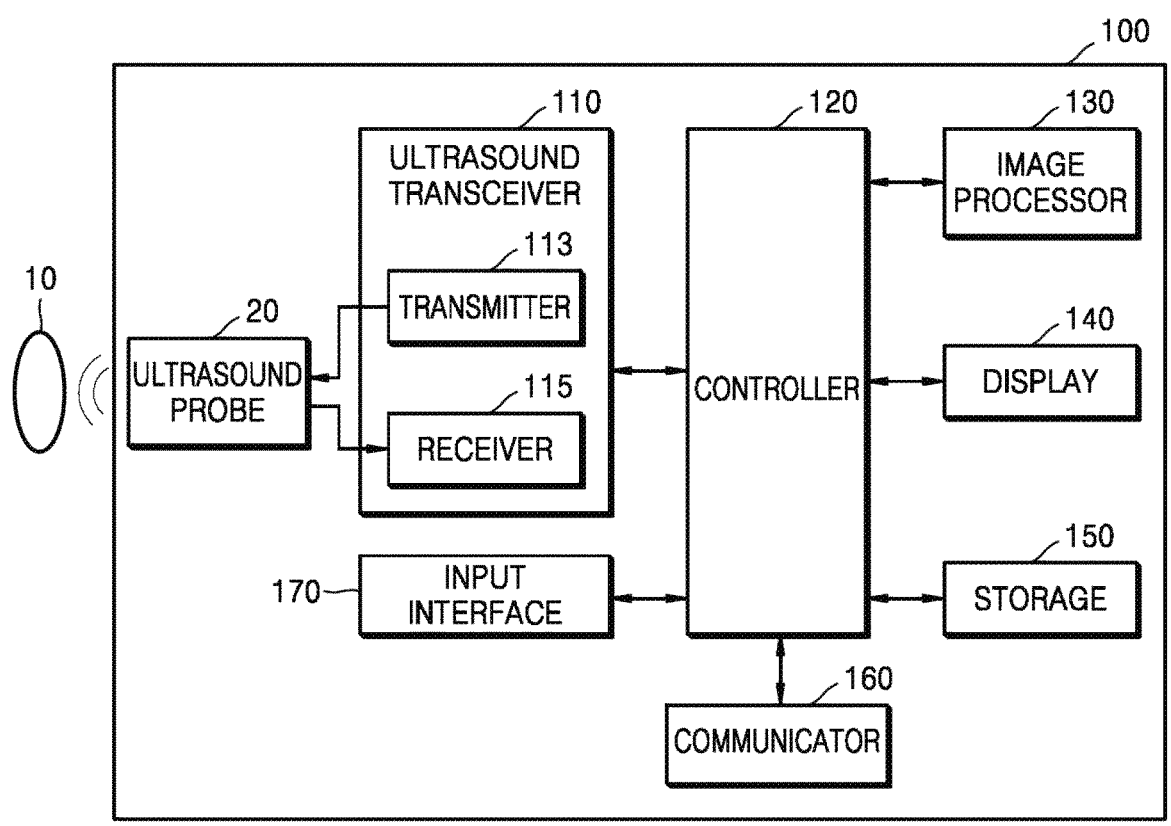
FIG. 1 is a block diagram illustrating an ultrasound diagnosis apparatus according to an embodiment.

Certain example embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of the example embodiments. Thus, it will be apparent that the example embodiments can be carried out without those specifically defined matters. Also, well-known functions or constructions are not described in detail since they would obscure example embodiments with unnecessary detail.

Terms such as "part" and "portion" used herein denote those that may be embodied by software or hardware. According to example embodiments, a plurality of parts or portions may be embodied by a single unit or element, or a single part or portion may include a plurality of elements.

In example embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound image data by converting reception signals received from the probe 20 from analogue to digital signals and summing the reception signals converted into digital form, based on a position and a focal point of the plurality of transducers.

The controller 120 may include at least one processor. The controller 120 generally controls overall operations of an ultrasound medical imaging apparatus 100. For example, the controller 120 may control a probe 20, an ultrasound transceiver 110, an image processor 130, a display 140, a storage 150, a communicator 160, and an input interface 170, by executing programs stored in the storage 150. Also, the controller 120 may perform functions of the ultrasound medical imaging apparatus illustrated with reference to FIGS. 3 to 13, by executing programs stored in the storage 150.

The controller 120 may generate ultrasound streaming image data of an object, based on ultrasound image data generated by the receiver 115.

When a preset event occurs, the controller 120 may generate ultrasound still image data based on the ultrasound image data. For example, when the controller 120 receives a control signal for freezing an ultrasound image of an object, the controller 120 may generate ultrasound still image data based on frozen ultrasound image. As another example, when the controller 120 receives a control signal for setting calipers on an ultrasound image of the object, the controller 120 may generate ultrasound still image data based on the ultrasound image on which the calipers are set. As another example, when the controller 120 receives a control signal for measuring at least a part of the object included in the ultrasound image, the controller 120 may generate ultrasound still image data including a measuring result value. As another example, when a result report including a result value of measuring at least a part of the object is displayed, the controller 120 may generate ultrasound still image data including the result report. As another example, when at least one of the ultrasound image data and the result report including the result value of measuring at least a part of the object is transferred to a server connected through a picture archiving and communication system (PACS), the controller 120 may generate ultrasound still image data including at least one of the ultrasound image data and the result report. As another example, when an ultrasound probe moves a predetermined number of times or less per unit time, the controller 120 may generate ultrasound still image data based on the ultrasound image of the object.

The controller 120 may check network environment (e.g., network bandwidth, performance of the external device, capability, network speed, etc.) between the ultrasound medical imaging apparatus 100 and an external device 200 in real-time. The controller 120 selects an appropriate representation based on the network environment, and controls the communicator 160 to sequentially transfer fragments of the selected representation to the external device 200.

The controller 120 may control the communicator 160 to transfer the ultrasound still image data to the external device 200 in priority over the ultrasound streaming image data, based on a bandwidth and transmission speed of a communication network between the ultrasound medical imaging apparatus 100 and the external device 200.

The image processor 130 may generate an ultrasound image by using ultrasound data generated from the ultrasound receiver 115. The controller 120 may perform functions of the image processor 130.

The display 140 may display a generated ultrasound image and various pieces of information processed by the ultrasound diagnosis apparatus 100. The ultrasound diagnosis apparatus 100 may include two or more displays 140 according to the present embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The communicator 160 may generate a communication network with the external device 200. The communicator 160 may transmit at least one of the ultrasound streaming image data and the ultrasound still image data to the external device 200.

The communicator 160 may transmit the ultrasound still image data and the ultrasound streaming image data to the external device 200 by respectively using separate communication ports.

The communicator 160 may transmit the ultrasound still image data to the external device 200 in priority over the ultrasound streaming image data, based on a bandwidth and transmission speed of a communication network between the ultrasound medical imaging apparatus 100 and the external device 200.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but embodiments are not limited thereto.

An example of the ultrasound diagnosis apparatus 100 according to the present embodiment is described below with reference to FIGS. 2A, 2B, and 2C.

FIGS. 2A, 2B, and 2C are diagrams illustrating ultrasound diagnosis apparatus according to an embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but embodiments are not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
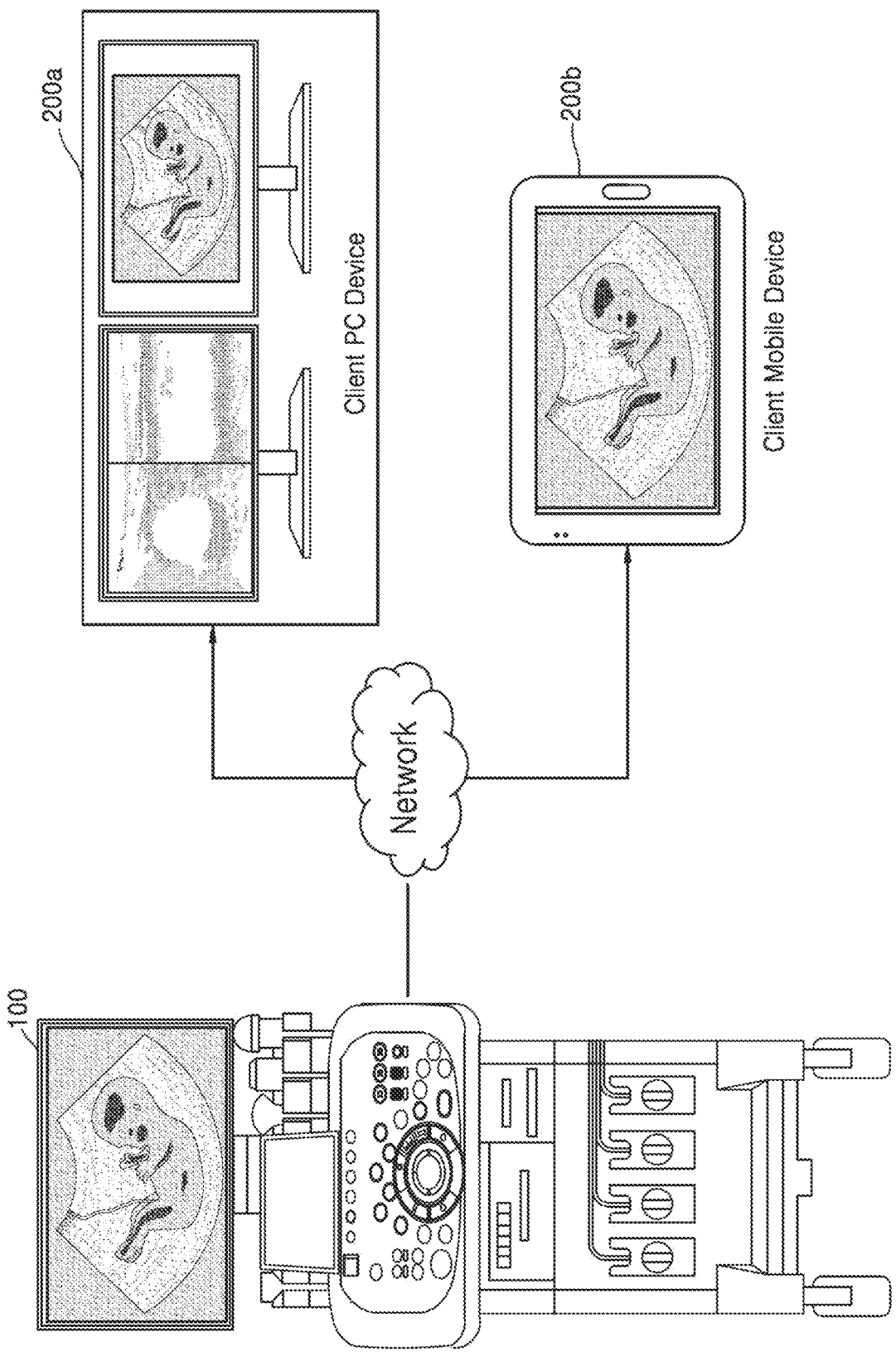
FIG. 3 is a diagram showing an example of transmitting ultrasound images by an ultrasound medical imaging apparatus to an external device, according to an embodiment.

FIG. 3 is a diagram showing an example of transmitting ultrasound images by the ultrasound medical imaging apparatus 100 to an external device, according to an embodiment.

Referring to FIG. 3, the ultrasound medical imaging apparatus 100 obtains ultrasound image data of an object, and transmits the ultrasound image data to external devices 200a and 200b via a communication network. The communication network may include a server for transmitting at least one piece of ultrasound image data in order for the ultrasound medical imaging apparatus 100 to transmit/receive data to/from the external devices 200a and 200b.

The ultrasound image data may include ultrasound streaming image data and ultrasound still image data. For example, the ultrasound imaging apparatus may include an ultrasound image displayed on the display of the ultrasound imaging apparatus 100. The ultrasound still image data may be generated based on the ultrasound image data when a preset event occurs. The ultrasound still image data may include the ultrasound image of the object generated by the ultrasound medical imaging apparatus 100. Also, the ultrasound still image data may include metadata about the object. The metadata may include information including images of the object and information including texts. The metadata may include information related to the ultrasound image, e.g., a location of a focal point, a depth of a focal point, and an inclination of an ultrasound wave irradiation surface. Also, the metadata may include information about a region of interest, e.g., a result value of measuring a size of at least a part of the object, an anatomical name of an organ, elasticity of a tissue, a location of a lesion, a size of the lesion, a shape of the lesion, and tissues around the lesion. Also, the metadata may include information regarding an ultrasound Doppler image, such as variance of a blood flow, a blood flow rate, colors corresponding to the blood flow rate, colors corresponding to blood flow directions, etc.

The external devices 200a and 200b may each include a display capable of displaying the ultrasound image based on the ultrasound image data. For example, the external device 200a may be a desktop personal computer (PC) and a laptop PC that is universally used. Also, the external device 200b may be a mobile device such as a mobile phone and a tablet PC.

The external devices 200a and 200b may display at least one ultrasound image based on the received ultrasound image data. For example, the external devices 200a and 200b may display at least one of an ultrasound streaming image and an ultrasound still image. The external devices 200a and 200b may display at least one of an ultrasound streaming image and an ultrasound still image, based on a user input. The external devices 200a and 200b may change a size of a region displaying at least one of the ultrasound streaming image and the ultrasound still image based on the user input. The external devices 200a and 200b may display a selected ultrasound still image based on a user input for selecting the ultrasound still image.

The ultrasound still image may have higher image quality than that of the ultrasound streaming image. For example, the ultrasound still image may have a higher resolution than that of at least one frame included in the ultrasound streaming image. As another example, the ultrasound still image may be greater in maximum brightness, average brightness, colorimetry, cadence, and clarity, and smaller in minimum brightness and noise than the frame included in the ultrasound streaming image. In detail, when the ultrasound image data is a signal, noise included in the ultrasound still image data generated based on the ultrasound image data may be less than noise included in at least one frame included in the ultrasound streaming image data generated based on the ultrasound image data. As another example, the ultrasound still image may have a lower compression rate than that of the ultrasound streaming image.

Figure 4:
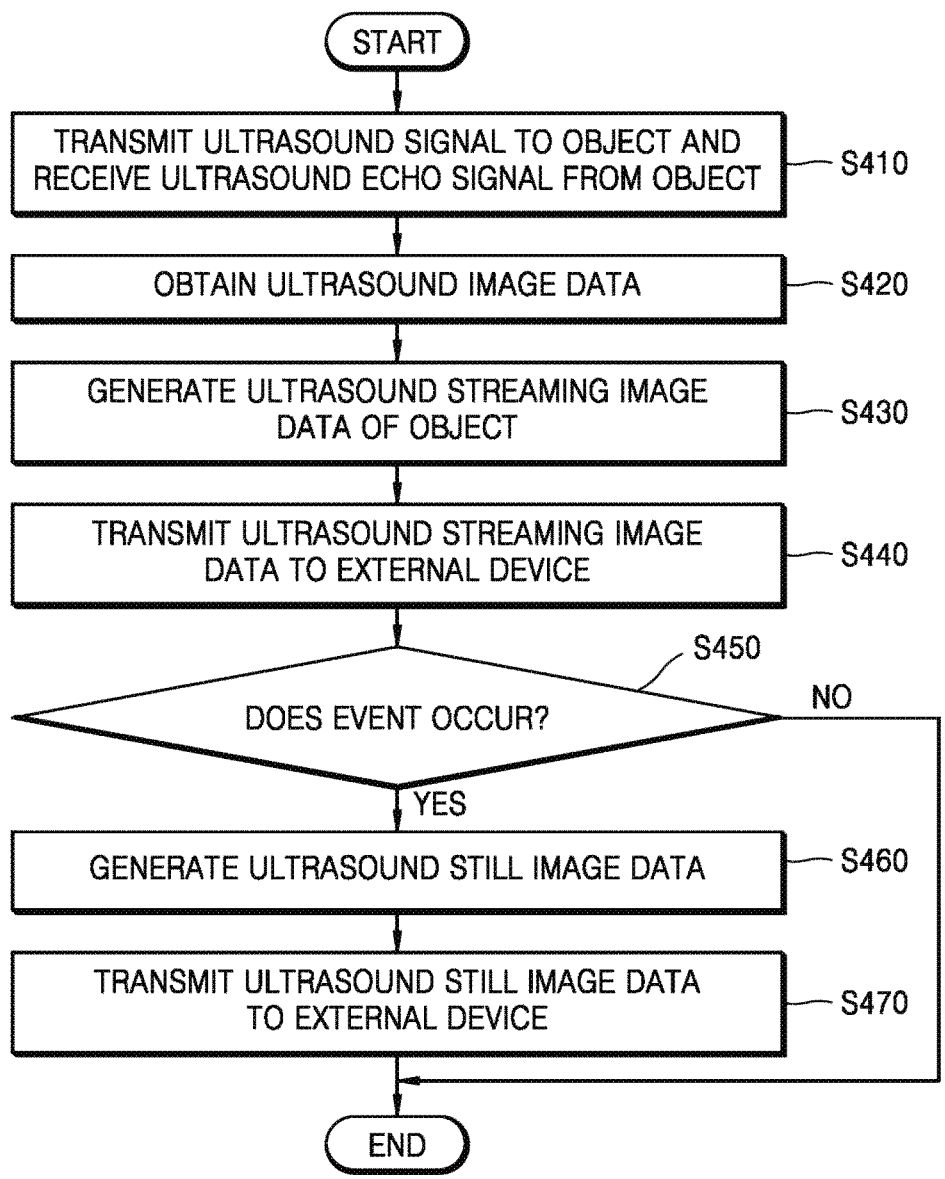
FIG. 4 is a flowchart illustrating a method of transmitting ultrasound streaming image data and ultrasound still image data, performed by an ultrasound medical imaging apparatus, to an external device, according to an embodiment.

FIG. 4 is a flowchart illustrating a method of transmitting ultrasound streaming image data and ultrasound still image data, performed by an ultrasound medical imaging, to an external device, according to an embodiment.

Referring to FIG. 4, the ultrasound medical imaging apparatus 100 transmits an ultrasound signal to the object and receives an ultrasound echo signal from the object (S410), obtains ultrasound image data by using the ultrasound echo signal (S420), generates ultrasound streaming image data about the object based on the ultrasound image data (S430), and transmits the ultrasound streaming image data to the external device 200 (S440). When a preset event occurs (S450), the ultrasound medical imaging apparatus 100 generates ultrasound still image data (S460), and transmits the ultrasound still image data to the external device 200 (S470).

In operation S410, the ultrasound medical imaging apparatus 100 transmits the ultrasound signal to an object 10 and receives the ultrasound echo signal from the object 10 by using an ultrasound probe.

In operation S420, the ultrasound medical imaging apparatus 100 may obtain the ultrasound image data by using the ultrasound echo signal.

In operation S430, the ultrasound medical imaging apparatus 100 may generate the ultrasound streaming image data based on the ultrasound image data.

According to an embodiment, the ultrasound medical imaging apparatus 100 may generate the ultrasound streaming image data based on an adaptive streaming mechanism technology. For example, the ultrasound medical imaging apparatus 100 may split ultrasound streaming image data into smaller units based on hypertext transfer protocol (HTTP). In detail, the ultrasound streaming image data may include representations and multimedia presentation description (MPD). The representations may be obtained by encoding ultrasound image data and component of the ultrasound image data under different conditions (e.g., network bandwidth, resolution, codec, etc.) The MPD may include information about periods that are obtained by splitting the ultrasound image data into a plurality of pieces, segments of a sufficiently short time period (e.g., 1 to 10 seconds) obtained by splitting a period, a file name, a sequence number, a start time, and length of each segment.

In operation S440, the ultrasound medical imaging apparatus 100 may transmit the generated ultrasound streaming image data to the external device 200.

The ultrasound medical imaging apparatus 100 may transmit the streaming image to the external device by using the adaptive streaming mechanism technology.

According to an embodiment, the ultrasound medical imaging apparatus 100 may check the network environment between the ultrasound medical imaging apparatus 100 and the external device (e.g., a bandwidth of the network, performance of the external device, capability, network speed, etc.) in real-time. The ultrasound medical imaging apparatus 100 may select an appropriate representation based on the network environment, and may transmit fragments of the selected representation sequentially to the external device 200.

According to an embodiment, the ultrasound medical imaging apparatus 100 may transmit the ultrasound streaming image data to the external device 200 after adjusting a bit rate of the ultrasound streaming image data according to the network environment. For example, the ultrasound medical imaging apparatus 100 may adjust a resolution of at least one frame included in the ultrasound streaming image according to the network environment. As another example, the ultrasound medical imaging apparatus 100 may adjust frames per second in the ultrasound streaming image data according to the network environment. Since the ultrasound medical imaging apparatus 100 adjusts the bit rate of the ultrasound streaming image data in real-time, the external device 200 may display the ultrasound streaming image without stuttering.

In operation S450, the ultrasound medical imaging apparatus 100 may determine whether the preset event occurs. The preset event includes input of a control signal for performing a certain function into the ultrasound medical imaging apparatus 100 from a user. Also, the preset event may include the ultrasound medical imaging apparatus 100 performing a certain function.

According to an embodiment, the ultrasound medical imaging apparatus 100 may determine whether the user inputs a control signal allowing the ultrasound medical imaging apparatus 100 to perform a certain function. For example, the ultrasound medical imaging apparatus 100 may determine whether a control signal for freezing the ultrasound image displayed on the ultrasound medical imaging apparatus 100 is input from the user. As another example, the ultrasound medical imaging apparatus 100 may determine whether a control signal for setting calipers on the ultrasound image displayed on the ultrasound medical imaging apparatus 100 is input from the user. As another example, the ultrasound medical imaging apparatus 100 may determine whether a control signal for measuring a size of at least a part of the object in the ultrasound image displayed on the ultrasound medical imaging apparatus 100 is input from the user. As another example, the ultrasound medical imaging apparatus 100 may determine whether a control signal for generating a result report including an ultrasound image diagnosis result is input from the user. As another example, the ultrasound medical imaging apparatus 100 may determine whether a control signal for transmitting at least one of ultrasound image data and the result report to a server connected through a picture archiving and communication system (PACS) is input from the user. As another example, it may be determined whether the ultrasound probe 20 moves a predetermined number of times per unit time or less.

According to an embodiment, the ultrasound medical imaging apparatus 100 may perform a certain function. For example, the ultrasound medical imaging apparatus 100 may perform a function of freezing the ultrasound image displayed on the ultrasound medical imaging apparatus 100. As another example, the ultrasound medical imaging apparatus 100 may perform a function of setting calipers on the ultrasound image. As another example, the ultrasound medical imaging apparatus 100 may measure a size of at least a part of the object in the ultrasound image. As another example, the ultrasound medical imaging apparatus 100 may generate a result report including an ultrasound image diagnosis result. As another example, the ultrasound medical imaging apparatus 100 may transmit at least one of ultrasound image data and the result report to a server connected through a PACS.

In operation S460, the ultrasound medical imaging apparatus 100 may generate ultrasound still image data based on occurrence of the preset event.

According to an embodiment, when the ultrasound medical imaging apparatus 100 receives the control signal for freezing the ultrasound image displayed on the ultrasound medical imaging apparatus 100, the ultrasound medical imaging apparatus 100 may generate ultrasound still image data including frozen ultrasound image. This will be described in more detail below referring to FIG. 5.

According to an embodiment, when the ultrasound medical imaging apparatus 100 receives the control signal for setting the caliper on the ultrasound image displayed on the ultrasound medical imaging apparatus 100, the ultrasound medical imaging apparatus 100 may generate ultrasound still image data including the ultrasound image on which the caliper is set. This will be described in more detail below referring to FIG. 6.

According to an embodiment, when the ultrasound medical imaging apparatus 100 receives a control signal for measuring at least a part of the object included in the ultrasound image, the controller 120 may generate ultrasound still image data including a measuring result value. Otherwise, when the ultrasound medical imaging apparatus 100 measures the size of at least a part of the object, the ultrasound medical imaging apparatus 100 may generate ultrasound still image data including a measurement result value. This will be described in more detail below referring to FIGS. 6 and 7.

According to an embodiment, when the ultrasound medical imaging apparatus 100 receives a control signal for generating a result report including the result value of measuring at least a part of the object, the ultrasound medical imaging apparatus 100 may generate ultrasound still image data including the result report. Otherwise, when the ultrasound medical imaging apparatus 100 generates the result report, the ultrasound medical imaging apparatus 100 may generate ultrasound still image data including the result report. This will be described in more detail below referring to FIG. 8.

According to an embodiment, the ultrasound medical imaging apparatus 100 receives a control signal for transmitting the result report including the ultrasound image data and the result value of measuring at least a part of the object to the server connected through the PACS, the ultrasound medical imaging apparatus 100 may generate ultrasound still image data including at least one of the ultrasound image and the result report. Alternatively, when the ultrasound medical imaging apparatus 100 transmits the result report to the server connected through the PACS, the ultrasound medical imaging apparatus 100 may generate the ultrasound still image data including at least one of the ultrasound image and the result report. This will be described in more detail below referring to FIG. 9.

According to an embodiment, when the ultrasound probe 20 moves a predetermined number of times per unit time or less, the ultrasound medical imaging apparatus 100 may generate ultrasound still image data including the ultrasound image displayed on the ultrasound medical imaging apparatus 100. This will be described in more detail below referring to FIG. 10.

According to an embodiment, when the ultrasound medical imaging apparatus 100 displays a result of computer aided diagnosis (CAD), the ultrasound medical imaging apparatus 100 may generate the ultrasound still image data including the CAD result. This will be described in more detail below referring to FIGS. 11 to 13.

In operation S470, the ultrasound medical imaging apparatus 100 may transmit the generated ultrasound still image data to the external device 200.

The bandwidth and transmission speed of the communication network formed between the ultrasound medical imaging apparatus 100 and the external device 200 may be restricted. Therefore, it may be difficult for the ultrasound medical imaging apparatus 100 to sufficiently transmit the ultrasound streaming image data and the ultrasound still image data to the external device 200. However, a doctor may need to see ultrasound images of high image quality for the remote treatment. In a case where the bandwidth and the transmission speed of the communication network are restricted, the ultrasound still image data generated when the preset event occurs is transmitted to the external device 200, and the doctor may easily perform the remote treatment.

According to an embodiment, the ultrasound medical imaging apparatus 100 may transmit the ultrasound streaming image data and the ultrasound still image data to the external device 200 by respectively using separate communication ports. For example, the ultrasound medical imaging apparatus 100 may transmit the ultrasound streaming image data to the external device 200 via a 7700 port, and may transmit the ultrasound still image data to the external device 200 via a 7800 port. However, above port numbers are examples, and one of ordinary skill would appreciate that the ports may be set differently according to a user and the network environment.

According to an embodiment, the ultrasound medical imaging apparatus 100 may transmit the ultrasound still image data to the external device 200, in priority over the ultrasound streaming image data. For example, the ultrasound medical imaging apparatus 100 may transmit the ultrasound still image data after stopping transmission of the ultrasound streaming image data. The ultrasound streaming image data that has been stopped to be transmitted may be continuously transmitted, after transmitting the ultrasound still image data. As another example, as described above, the ultrasound medical imaging apparatus 100 may transmit the ultrasound streaming image data and the ultrasound still image data to the external device 200 by using separate communication ports. The ultrasound medical imaging apparatus 100 may transmit the ultrasound still image data to the external device 200 in priority over the ultrasound streaming image data, by granting priority to the port through which the ultrasound still image data is transmitted. By transmitting the ultrasound still image to the external device 200 with priority, the doctor may conveniently perform the remote treatment even when the bandwidth and the transmission speed of the ultrasound communication network are restricted.

According to an embodiment, the ultrasound medical imaging apparatus 100 may transmit the ultrasound still image to the external device 200 in priority over the ultrasound streaming image, based on the bandwidth and the transmission speed of the communication network provided between the ultrasound medical imaging apparatus 100 and the external device 200. The ultrasound medical imaging apparatus 100 may determine whether the bandwidth and the transmission speed of the communication network are available to simultaneously transmit the ultrasound streaming image and the ultrasound still image to the external device 200. The ultrasound medical imaging apparatus 100 may transmit the ultrasound still image to the external device 200 in priority over the ultrasound streaming image, based on a determination result that the ultrasound streaming image and the ultrasound still image may not be simultaneously transmitted. Alternatively, the ultrasound medical imaging apparatus 100 may transmit the ultrasound streaming image to the external device 200 by decreasing a bit rate of the ultrasound streaming image. For example, the ultrasound medical imaging apparatus 100 may transmit the ultrasound streaming image to the external device 200 after reducing a resolution of the ultrasound streaming image. As another example, the ultrasound medical imaging apparatus 100 may transmit the ultrasound streaming image to the external device 200 after increasing a compression rate of the ultrasound streaming image.

Figure 5:
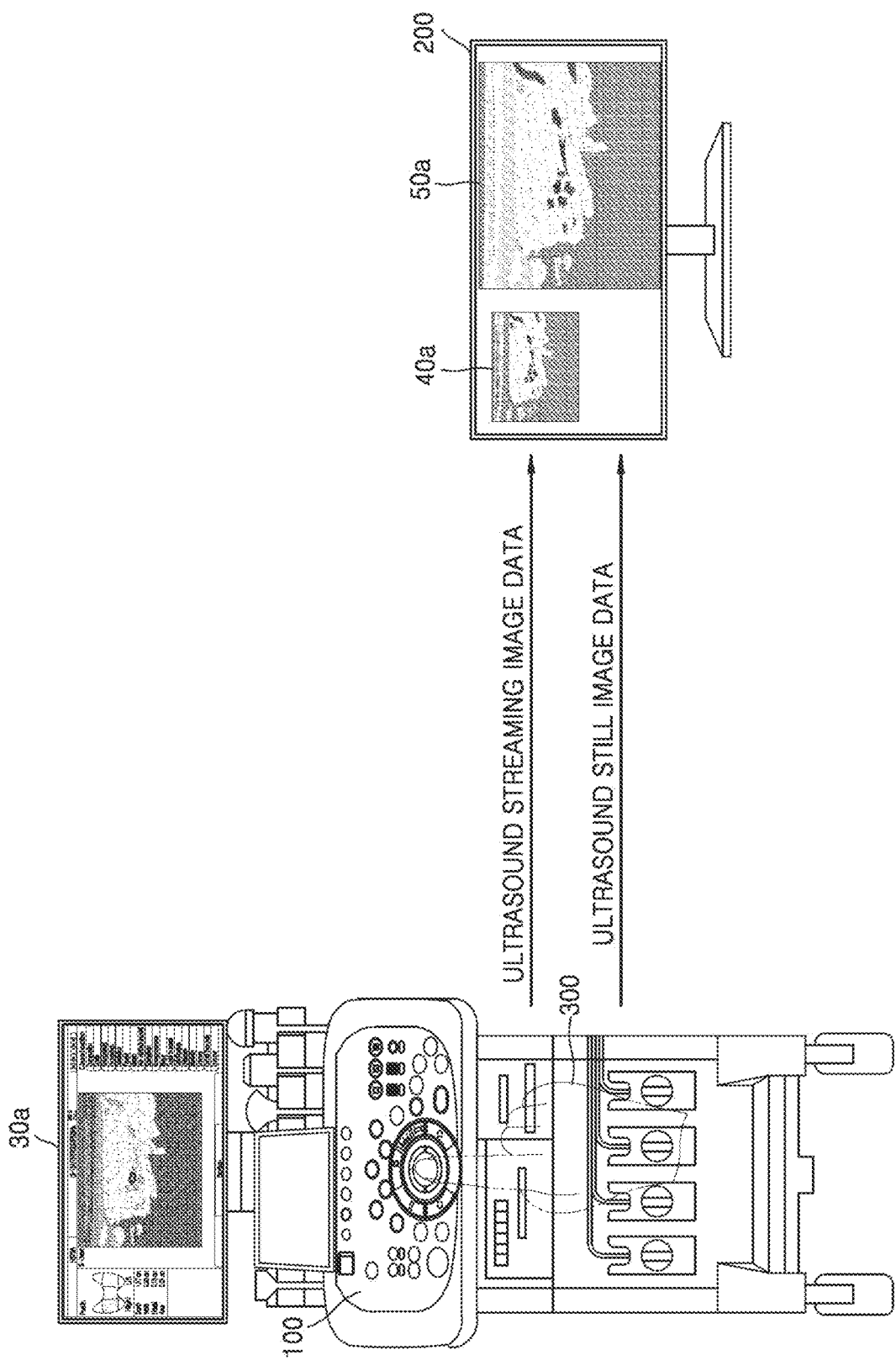
FIG. 5 is a diagram of an example of transmitting ultrasound streaming image data and ultrasound still image data, performed by an ultrasound medical imaging apparatus, to an external device, according to an embodiment.

FIG. 5 is a diagram of an example of transmitting ultrasound streaming image data and ultrasound still image data, performed by the ultrasound medical imaging apparatus 100, to an external device, according to an embodiment.

Referring to FIG. 5, the ultrasound medical imaging apparatus 100 may obtain ultrasound image data about the object in real-time. The ultrasound medical imaging apparatus 100 may store the obtained ultrasound image data in the storage in real-time, after applying an index to each frame. Also, the ultrasound medical imaging apparatus 100 may display ultrasound images of the object in real-time by using the obtained ultrasound image data.

The ultrasound medical imaging apparatus 100 may generate the ultrasound streaming image data of the object based on the ultrasound image data. The ultrasound medical imaging apparatus 100 may transmit the ultrasound streaming image data to the external device 200.

The ultrasound medical imaging apparatus 100 may receive a control signal for freezing an ultrasound image 30*a* displayed on the ultrasound medical imaging apparatus 100 from a user 300. The ultrasound medical imaging apparatus 100 may freeze the ultrasound image 30*a* based on the control signal. For example, when receiving the control signal, the ultrasound medical imaging apparatus 100 may stop transmitting an ultrasound signal to the object and receiving an ultrasound echo signal from the object. The ultrasound medical imaging apparatus 100 provides indexes of the frames stored in the storage, and reads a frame corresponding to a selected index from the storage based on an input of selecting one of the indexes from the user, in order to display the frame as a frozen image. As another example, when receiving a control signal, the ultrasound medical imaging apparatus 100 may display last displayed frame of the ultrasound image 30a as a frozen image.

The ultrasound medical imaging apparatus 100 may generate ultrasound still image data including a frozen image, when receiving the control signal for freezing the ultrasound image 30a. The ultrasound medical imaging apparatus 100 may transmit the ultrasound still image data to the external device 200.

The external device 200 may display an ultrasound streaming image 40a based on the ultrasound streaming image data transmitted from the ultrasound medical imaging apparatus 100. Also, the external device 200 may display an ultrasound still image 50a based on the ultrasound still image data.

When the ultrasound image is frozen, the ultrasound medical imaging apparatus 100 may generate ultrasound streaming image data based on the frozen ultrasound image 30a and may transmit the ultrasound streaming image data to the external device 200. Image quality of an ultrasound streaming image 40a may degrade according to the network environment of the communication network between the ultrasound medical imaging apparatus 100 and the external device 200. However, since an ultrasound still image 50a of high image quality is displayed, the doctor may easily perform the remote treatment.

Figure 6:
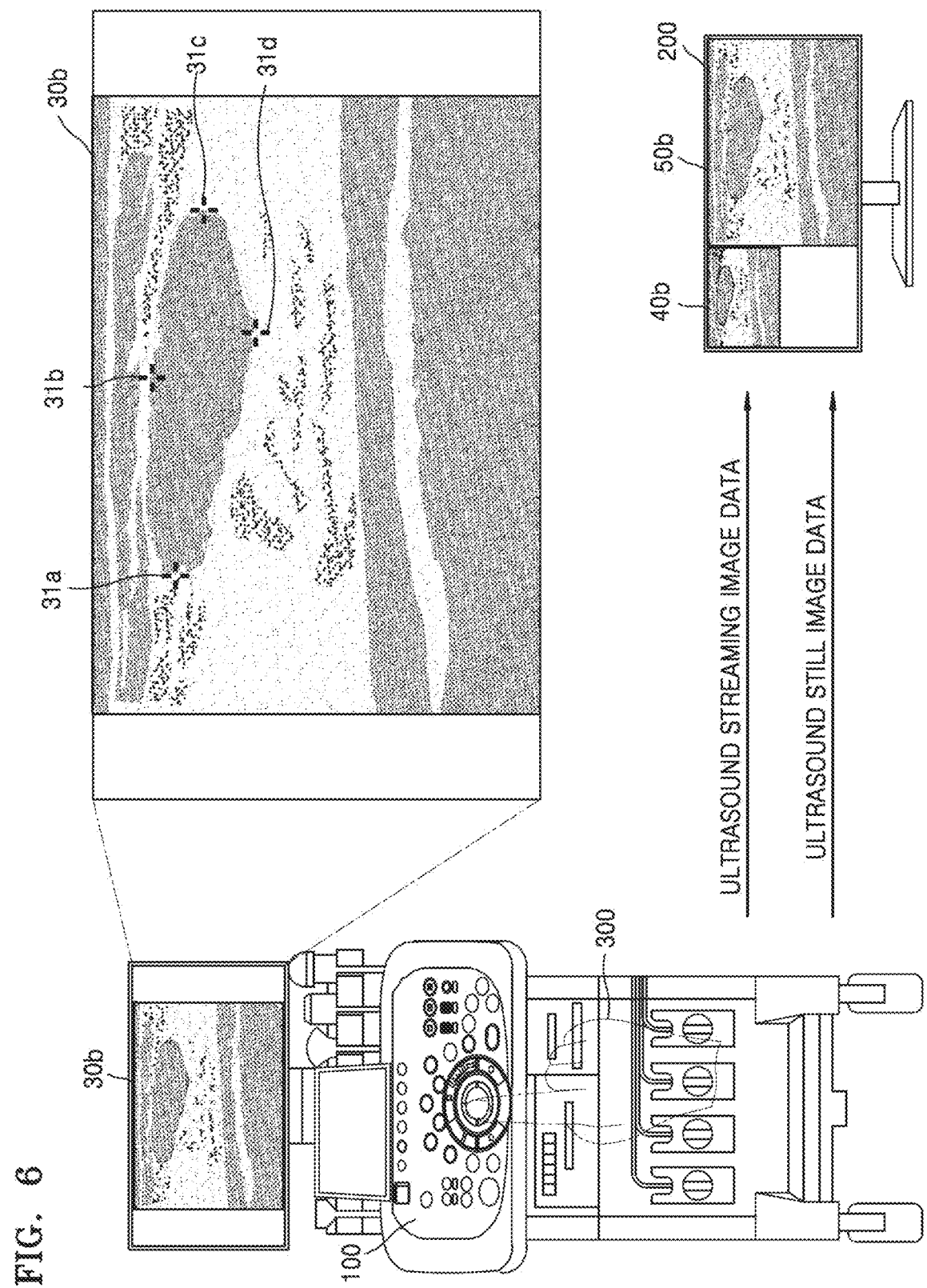
FIG. 6 is a diagram of an example of transmitting ultrasound streaming image data and ultrasound still image data, performed by an ultrasound medical imaging apparatus, to an external device, according to an embodiment.

FIG. 6 is a diagram of an example of transmitting ultrasound streaming image data and ultrasound still image data, performed by the ultrasound medical imaging apparatus 100, to an external device, according to an embodiment.

Referring to FIG. 6, the ultrasound medical imaging apparatus 100 may receive a control signal for setting calipers on the ultrasound image of the object from the user 300. The ultrasound medical imaging apparatus 100 may set calipers 31a, 31b, 31c, and 31d on an ultrasound image 30b based on the received control signal. For example, the ultrasound medical imaging apparatus 100 may receive a control signal for setting calipers on a region of interest in the ultrasound image from the user 300. The region of interest may be a region that seems to be a lesion.

Also, when setting of the caliper is finished, the ultrasound medical imaging apparatus 100 may receive from the user a control signal for measuring a size of the region of interest by using the set caliper. The region of interest may be at least a part of the object for measuring a size (e.g., CRL of a fetus, NT, IT, HC of a brain, BPD, OFD, Vp, TCD, CM, Femur, Tibia, Fibula, Ulna, Radius, and Humerus of a bone, intima-media thickness of a blood vessel, an area or a volume of a plug in a blood vessel, etc.)

According to an embodiment, when receiving a control signal for setting the calipers 31a, 31b, 31c, and 31d on the ultrasound image displayed on the ultrasound medical imaging apparatus 100, the ultrasound medical imaging apparatus 100 may generate ultrasound still image data including the ultrasound image on which the calipers 31a, 31b, 31c, and 31d are set.

According to an embodiment, when the ultrasound medical imaging apparatus 100 receives a control signal for measuring at least a part of the object included in the ultrasound image, the controller 120 may generate ultrasound still image data including a measuring result value.

The ultrasound medical imaging apparatus 100 may transmit the ultrasound still image data to the external device 200.

The external device 200 may display an ultrasound streaming image 40b based on the ultrasound streaming image data transmitted from the ultrasound medical imaging apparatus 100. Also, the external device 200 may display an ultrasound still image 50b based on the ultrasound still image data.

The doctor has to identify whether the calipers are set on right positions in the region of interest. Image quality of the ultrasound streaming image 40b may degrade according to the network environment of the communication network between the ultrasound medical imaging apparatus 100 and the external device 200. However, since the ultrasound still image 50b of high image quality is displayed, the doctor may easily identify whether the calipers 31a, 31b, 31c, and 31d are set on right positions.

Figure 7:
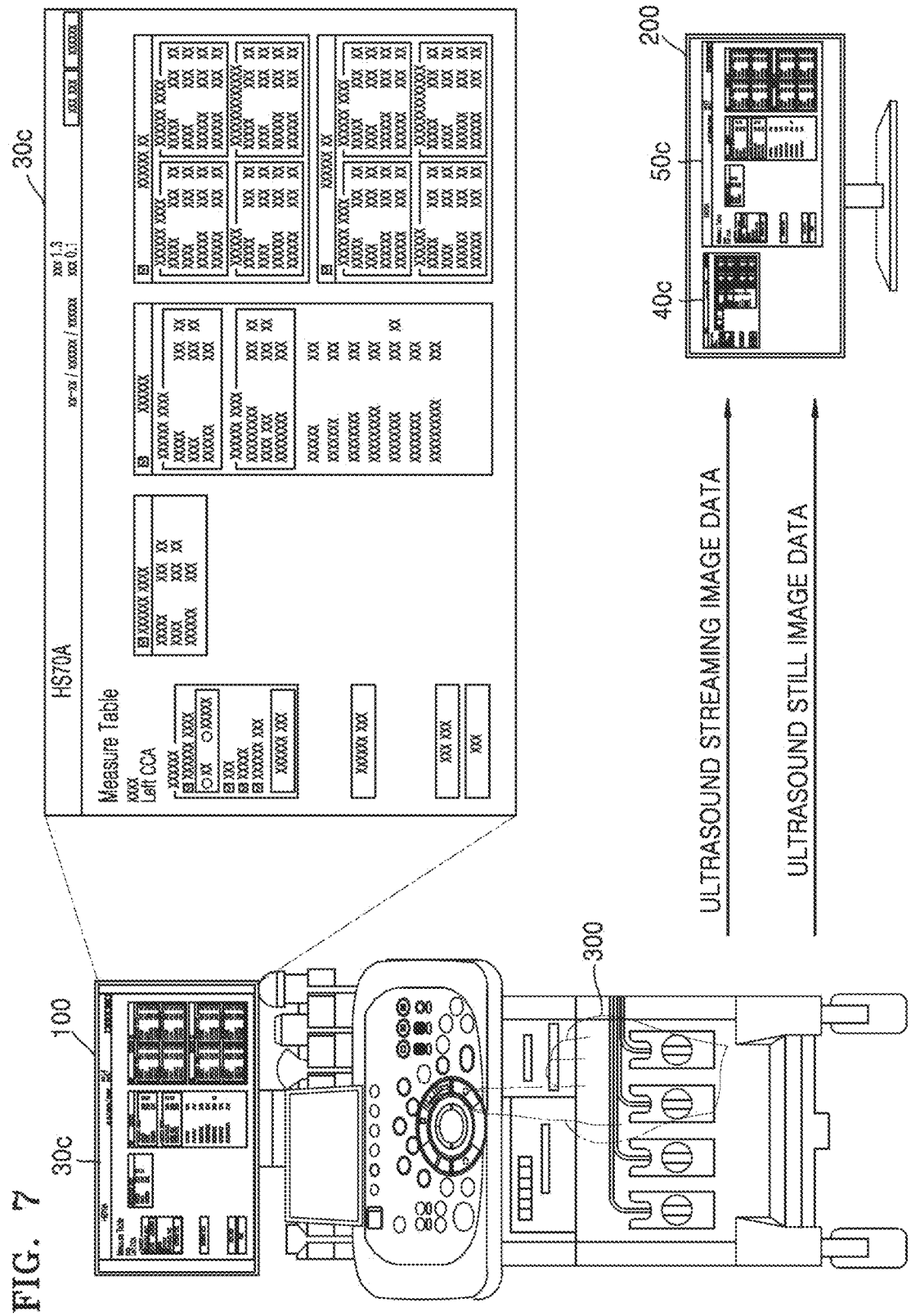
FIG. 7 is a diagram of an example of transmitting ultrasound streaming image data and ultrasound still image data, performed by an ultrasound medical imaging apparatus, to an external device, according to an embodiment.

FIG. 7 is a diagram of an example of transmitting ultrasound streaming image data and ultrasound still image data, performed by the ultrasound medical imaging apparatus 100, to an external device, according to an embodiment.

Referring to FIG. 7, the ultrasound medical imaging apparatus 100 may generate ultrasound still image data including a result value of measuring a size of at least a part of the object included in the ultrasound image.

The ultrasound medical imaging apparatus 100 may receive a control signal for measuring a size of at least a part of the object included in the ultrasound image from the user. For example, as described above with reference to FIG. 6, the control signal may be a signal representing that the setting of calipers on the ultrasound image is finished. As another example, the control signal may be a signal for detecting the object in the ultrasound image and detecting a size of at least a part of the object (e.g., CRL of a fetus, NT, IT, HC of a brain, BPD, OFD, Vp, TCD, CM, Femur, Tibia, Fibula, Ulna, Radius, and Humerus of a bone, intima-media thickness of a blood vessel, an area or a volume of a plug in a blood vessel, etc.) by using the CAD.

The ultrasound medical imaging apparatus 100 may measure the size of at least a part of the object in response to the control signal. Also, the ultrasound medical imaging apparatus 100 may display an ultrasound image 30c including the measuring result value.

According to an embodiment, the ultrasound medical imaging apparatus 100 may generate ultrasound still image data including the result value of measuring the size of at least a part of the object. The ultrasound still image data may include the measuring result value on ultrasound image data about the object. Alternatively, the ultrasound streaming image data may include the measuring result value as a table format as shown in FIG. 7.

According to an embodiment, the ultrasound medical imaging apparatus 100 may generate ultrasound still image data including a measuring result value as a text data format. When the measuring result value is included in the ultrasound still image data as the text data format, the ultrasound still image data of smaller size than the ultrasound still image data including the measuring result value as an image data format may be generated. Also, since the external device 200 receives the ultrasound still image data including the measuring result value as the text data format, the external device 200 may clearly display the measuring result value.

The ultrasound medical imaging apparatus 100 may transmit the ultrasound still image data including the measuring result value to the external device 200.

The external device 200 may display an ultrasound streaming image 40c including the measuring result value, based on the ultrasound streaming image data transmitted from the ultrasound medical imaging apparatus 100. Also, the external device 200 may display an ultrasound still image 50c including the measuring result value based on the ultrasound still image data.

Image quality of the ultrasound streaming image 40c may degrade according to the network environment of the communication network between the ultrasound medical imaging apparatus 100 and the external device 200. However, since the ultrasound still image 50c of high image quality is displayed, the doctor may identify the result value of measuring at least a part of the object.

Figure 8:
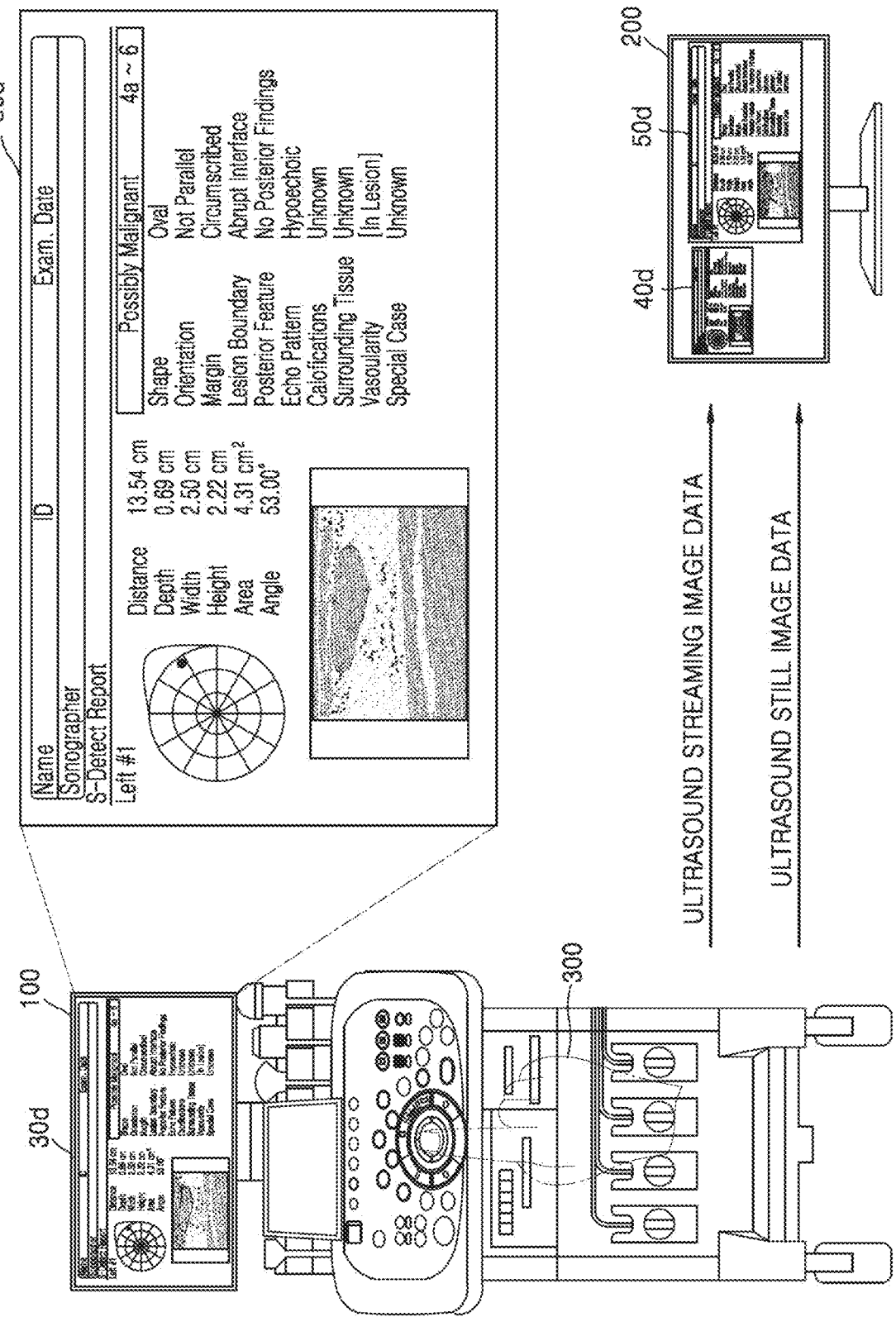
FIG. 8 is a diagram of an example of transmitting ultrasound streaming image data and ultrasound still image data, performed by an ultrasound medical imaging apparatus, to an external device, according to an embodiment.

FIG. 8 is a diagram of an example of transmitting ultrasound streaming image data and ultrasound still image data, performed by the ultrasound medical imaging apparatus 100, to an external device, according to an embodiment.

Referring to FIG. 8, the ultrasound medical imaging apparatus 100 may generate a result report 30d including the result value of measuring the size of at least a part of the object included in the ultrasound image. The ultrasound medical imaging apparatus 100 may display the result report 30d. The ultrasound medical imaging apparatus 100 may generate ultrasound still image data including the result report 30d.

For example, as shown in FIG. 8, the ultrasound medical imaging apparatus 100 may display the result report 30d about breast lesions of the object. In detail, the result report 30d may include information related to the ultrasound image, e.g., that the ultrasound image shows which part of the object, a location of a focal point, a depth of the focal point, an inclination of an ultrasound irradiation surface of the ultrasound probe 20, etc. Also, the result report 30d may include information related to the lesion, e.g., a location of the lesion, a size of the lesion, a shape of the lesion, and tissues around the lesion. The result report 30d may include the ultrasound image. The result report 30d may include the measuring result value as a table format.

According to an embodiment, the ultrasound medical imaging apparatus 100 may generate the ultrasound still image data including the result report 30d at least a part of which is included as a test data format.

The ultrasound medical imaging apparatus 100 may transmit the ultrasound still image data including the result report to the external device 200.

The external device 200 may display an ultrasound streaming image 40d including the measuring result value, based on the ultrasound streaming image data transmitted from the ultrasound medical imaging apparatus 100. Also, the external device 200 may display an ultrasound still image 50d including the measuring result value based on the ultrasound still image data.

Image quality of the ultrasound streaming image 40d may degrade according to the network environment of the communication network between the ultrasound medical imaging apparatus 100 and the external device 200. However, since an ultrasound still image 50d of high image quality is displayed, the doctor may easily identify the result report 30d.

Figure 9:
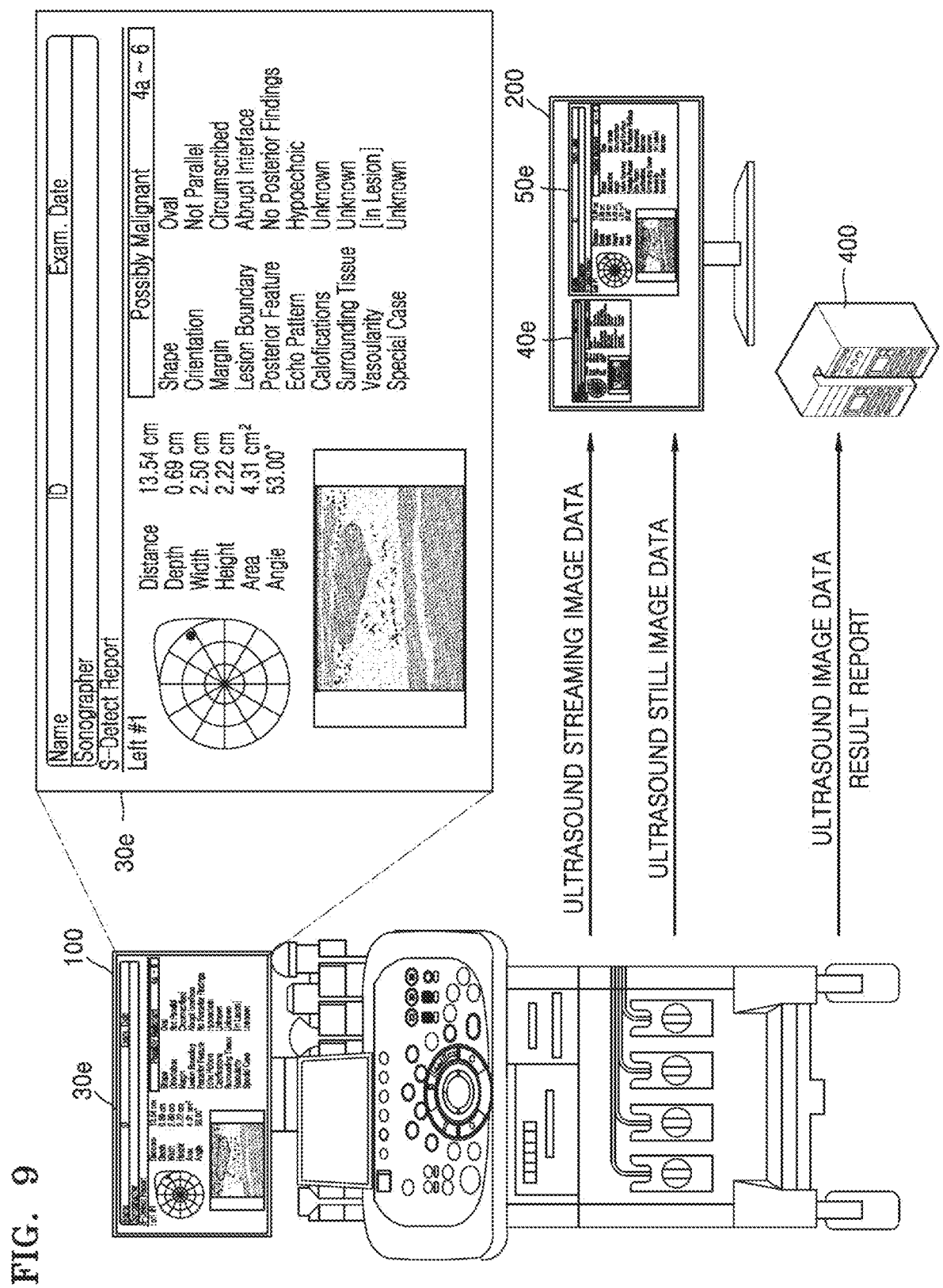
FIG. 9 is a diagram of an example of transmitting ultrasound streaming image data and ultrasound still image data, performed by an ultrasound medical imaging apparatus, to an external device, according to an embodiment.

FIG. 9 is a diagram of an example of transmitting ultrasound streaming image data and ultrasound still image data, performed by the ultrasound medical imaging apparatus 100, to an external device, according to an embodiment.

Referring to FIG. 9, the ultrasound medical imaging apparatus 100 may transmit a result report 30e including ultrasound image data and a result value of measuring at least a part of the object to a server 400 connected through the PACS. The ultrasound medical imaging apparatus 100 may receive a control signal from the user and transmit the result report 30e to the server 400. For example, the ultrasound medical imaging apparatus 100 may receive a control signal from the user for transmitting the ultrasound image data and the result report 30e to the server 400. As another example, when receiving a control signal representing diagnosis completion from the user, the ultrasound medical imaging apparatus 100 may transmit the result report 30e to the server 400.

According to an embodiment, when receiving a control signal, the ultrasound medical imaging apparatus 100 may generate ultrasound still image data including at least one of the ultrasound image and the result report 30e.

According to an embodiment, when the ultrasound medical imaging apparatus 100 transmits the result report 30e to the server 400, the ultrasound medical imaging apparatus 100 may generate ultrasound still image data including at least one of the ultrasound image and the result report 30e.

The ultrasound medical imaging apparatus 100 may transmit the ultrasound still image data including at least one of the ultrasound image and the result report 30e to the external device 200.

The external device 200 may display an ultrasound streaming image 40d including the measuring result value, based on the ultrasound streaming image data transmitted from the ultrasound medical imaging apparatus 100. Also, the external device 200 may display an ultrasound still image 50e including the measuring result value based on the ultrasound still image data.

Image quality of the ultrasound streaming image 40e may degrade according to the network environment of the communication network between the ultrasound medical imaging apparatus 100 and the external device 200. However, since an ultrasound still image 50e of high image quality is displayed, the doctor may easily identify at least one of the ultrasound image and the result report 30e.

Figure 10:
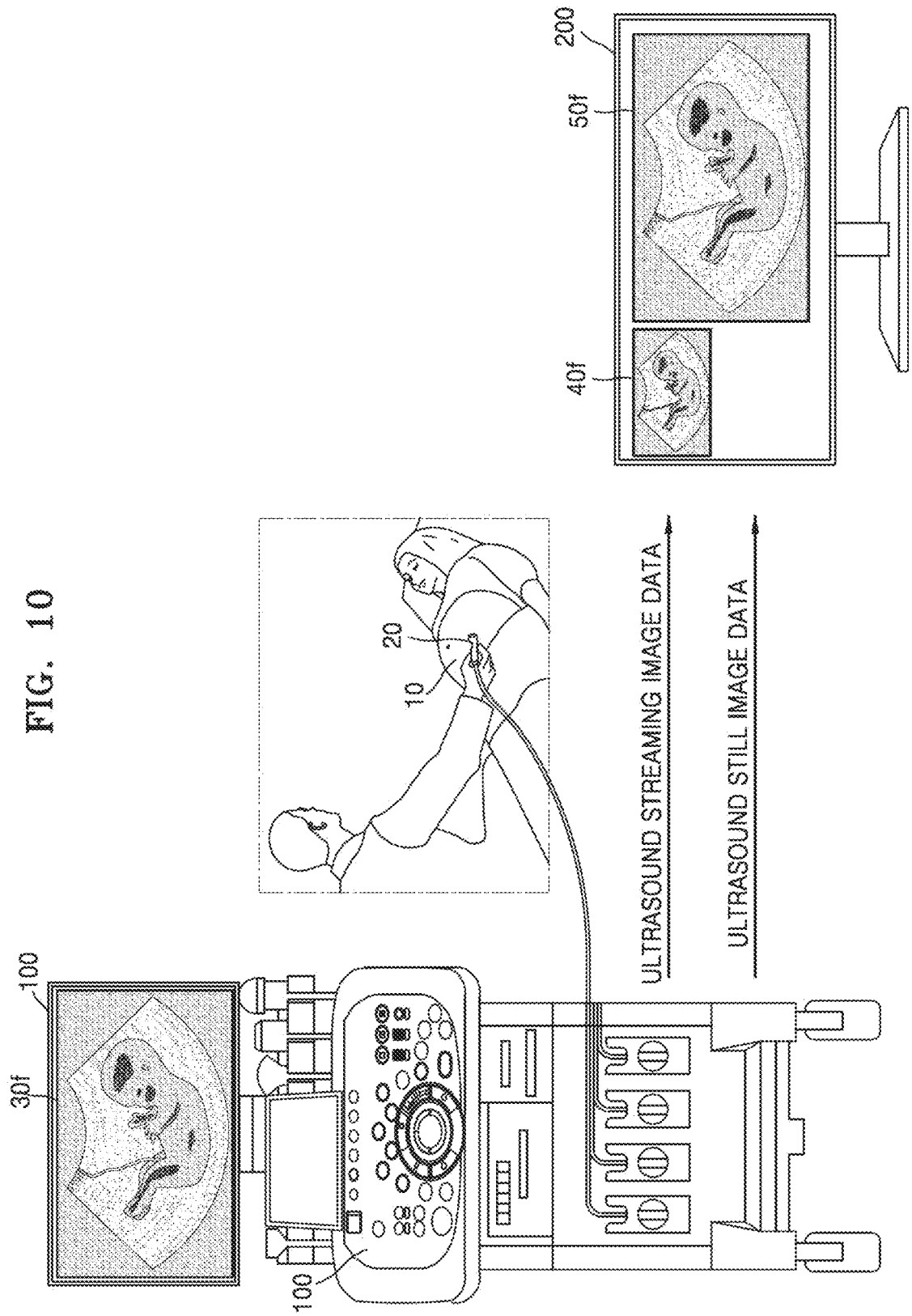
FIG. 10 is a diagram of an example of transmitting ultrasound streaming image data and ultrasound still image data, performed by an ultrasound medical imaging apparatus, to an external device, according to an embodiment.

FIG. 10 is a diagram of an example of transmitting ultrasound streaming image data and ultrasound still image data, performed by the ultrasound medical imaging apparatus 100, to an external device, according to an embodiment.

Referring to FIG. 10, the ultrasound medical imaging apparatus 100 may detect the number of movements of the ultrasound probe 20 per unit time. When the number of movements of the ultrasound probe 20 per unit time is equal to or less than a reference that is set in advance, the ultrasound medical imaging apparatus 100 may determine that the user observes the region of interest.

According to an embodiment, when the ultrasound probe 20 moves the reference number of times or less per unit time, the ultrasound medical imaging apparatus 100 may generate the ultrasound still image data based on an ultrasound image 30f of the object. For example, when the ultrasound probe 20 moves three times or less per five seconds, the ultrasound medical imaging apparatus 100 may generate ultrasound still image data.

The ultrasound medical imaging apparatus 100 may transmit the ultrasound streaming image data and the ultrasound still image data to the external device 200.

The external device 200 may display an ultrasound streaming image 40f based on the ultrasound streaming image data transmitted from the ultrasound medical imaging apparatus 100. Also, the external device 200 may display an ultrasound still image 50f based on the ultrasound still image data.

Image quality of the ultrasound streaming image 40f may degrade according to the network environment of the communication network between the ultrasound medical imaging apparatus 100 and the external device 200. However, since the ultrasound still image 50f of high image quality is displayed, the doctor may easily perform the remote treatment.

Figure 11:
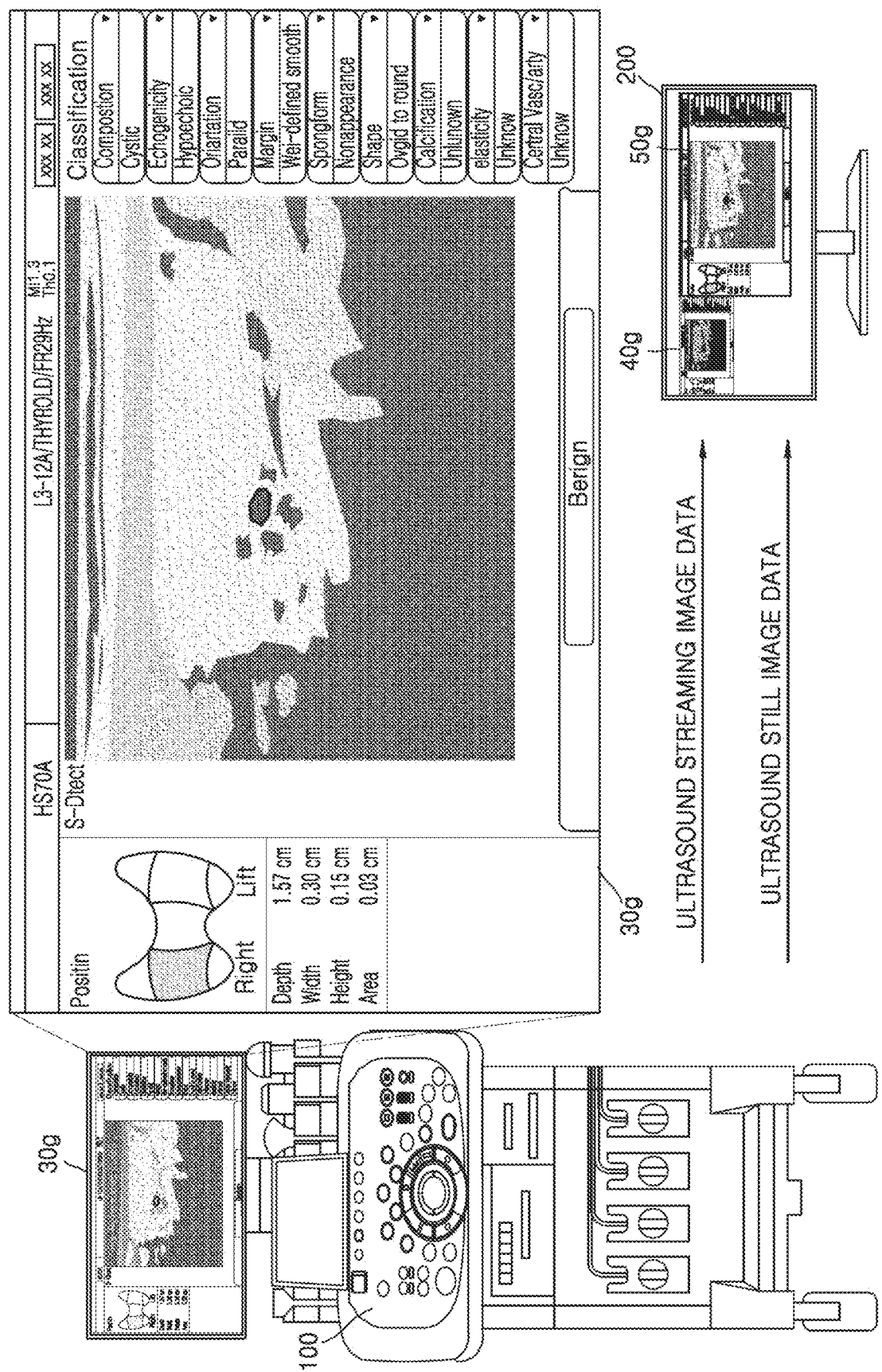
FIG. 11 is a diagram of an example of transmitting ultrasound streaming image data and ultrasound still image data, performed by an ultrasound medical imaging apparatus, to an external device, according to an embodiment.

FIG. 11 is a diagram of an example of transmitting ultrasound streaming image data and ultrasound still image data, performed by the ultrasound medical imaging apparatus 100, to an external device, according to an embodiment.

Referring to FIG. 11, the ultrasound medical imaging apparatus 100 may display a CAD result.

The ultrasound medical imaging apparatus 100 may detect a lesion by using the CAD and display the detection result. As another example, the ultrasound medical imaging apparatus 100 may detect and display a size of at least a part of the object (e.g., CRL of a fetus, NT, IT, HC of a brain, BPD, OFD, Vp, TCD, CM, Femur, Tibia, Fibula, Ulna, Radius, and Humerus of a bone, intima-media thickness of a blood vessel, an area or a volume of a plug in a blood vessel, etc.) from the ultrasound image.

The ultrasound medical imaging apparatus 100 may receive a control signal from the user and may execute a preset CAD function. For example, the ultrasound medical imaging apparatus 100 may receive a control signal for executing the CAD function for detecting the lesion from the user, and detect the lesion. As another example, the ultrasound medical imaging apparatus 100 may receive a control signal from the user for executing the CAD function that detects a size of at least a part of the object, and detect the lesion.

The ultrasound medical imaging apparatus 100 may display the result of executing the CAD function. For example, the ultrasound medical imaging apparatus 100 may detect the lesion from the ultrasound image of the object, analyze the detected lesion, and display the analysis result. Referring to FIG. 11, the ultrasound medical imaging apparatus 100 may detect a lesion from an ultrasound image of a thyroid, and display a result 30g of analyzing the lesion.

In detail, the ultrasound medical imaging apparatus 100 may display information related to the ultrasound image, e.g., that the ultrasound image shows which part of the object, a location of a focal point, a depth of the focal point, an inclination of an ultrasound irradiation surface of the ultrasound probe 20, etc. Also, the ultrasound medical imaging apparatus 100 may display information related to the lesion, e.g., a location of the lesion, a size of the lesion, a shape of the lesion, and tissues around the lesion.

The ultrasound medical imaging apparatus 100 may generate ultrasound still image data including the result 30g of performing the CAD function. The ultrasound medical imaging apparatus 100 may generate ultrasound still image data including the result 30g of performing the CAD function as a text data format.

The ultrasound medical imaging apparatus 100 may transmit ultrasound still image data including the result 30g of performing the CAD function to the external device 200.

The external device 200 may display an ultrasound streaming image 40g including the result 30g of performing the CAD function, based on the ultrasound streaming image data transmitted from the ultrasound medical imaging apparatus 100. Also, the external device 200 may display an ultrasound still image 50g including the result 30g of performing the CAD function, based on the ultrasound still image data.

Image quality of the ultrasound streaming image 40g may degrade according to the network environment of the communication network between the ultrasound medical imaging apparatus 100 and the external device 200. However, since the ultrasound still image 50g of high image quality is displayed, the doctor may identify the result value of measuring at least a part of the object.

Figure 12:
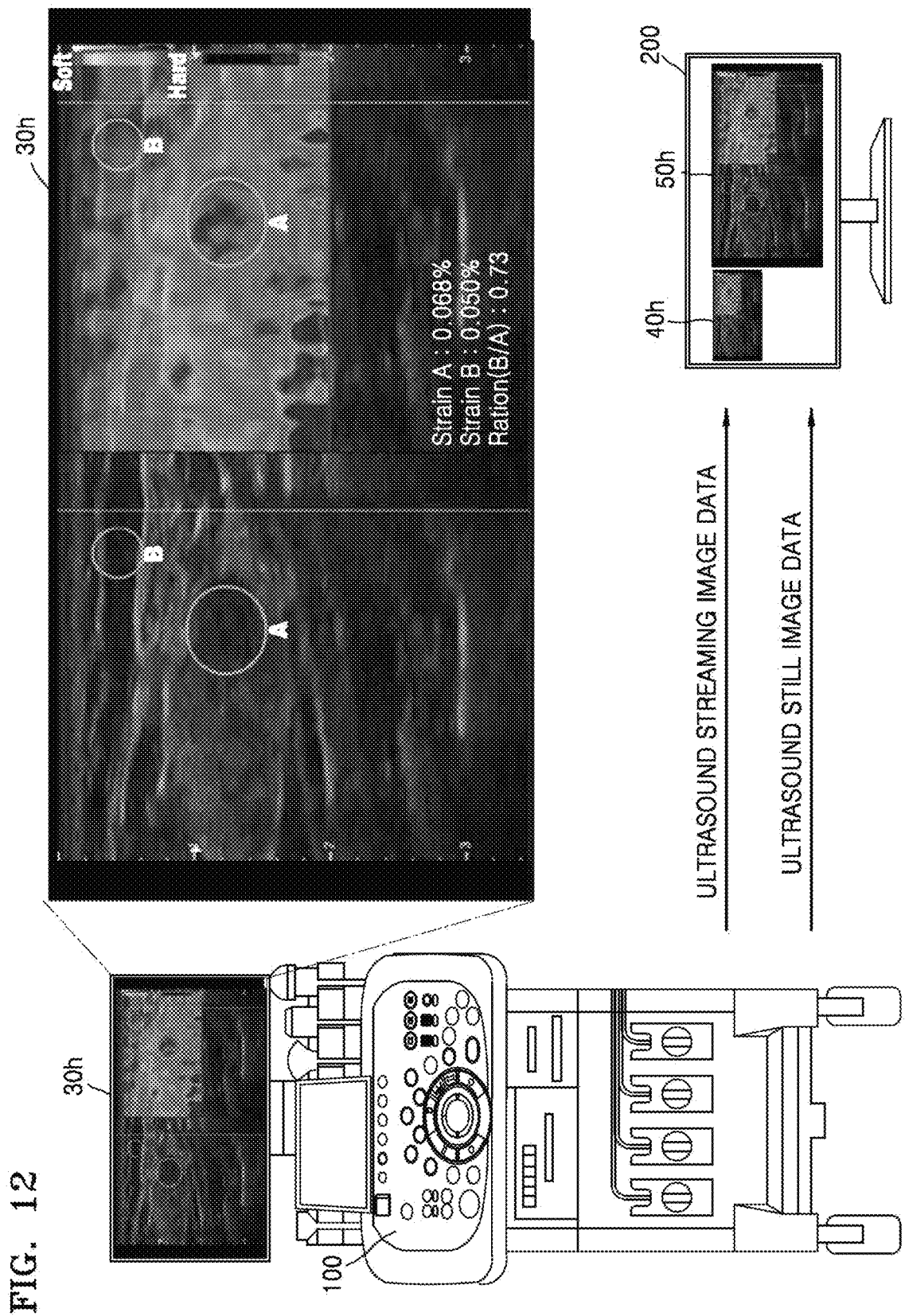
FIG. 12 is a diagram of an example of transmitting ultrasound streaming image data and ultrasound still image data, performed by an ultrasound medical imaging apparatus, to an external device, according to an embodiment.

FIG. 12 is a diagram of an example of transmitting ultrasound streaming image data and ultrasound still image data, performed by the ultrasound medical imaging apparatus 100, to an external device, according to an embodiment.

The ultrasound medical imaging apparatus 100 may display a result 30h of detecting a lesion from the ultrasound image of the object by using the CAD function. In detail, as shown in FIG. 12, the ultrasound medical imaging apparatus 100 may detect strain of a region A that is suspected as a lesion and strain of a region B that is breast fat, from an ultrasound image of a breast. The ultrasound medical imaging apparatus 100 may calculate a ratio between the strains of the region A and the region B. The ultrasound medical imaging apparatus 100 may detect the region A as the lesion based on the calculated ratio.

The ultrasound medical imaging apparatus 100 may display a result of analyzing the detected lesion. Displaying of the result of analyzing the lesion is described above with reference to FIGS. 7, 8, and 11, and detailed descriptions of overlapping elements are omitted.

The ultrasound medical imaging apparatus 100 may generate ultrasound still image data including at least one of the result 30h of detecting the lesion by the CAD function and the result of analyzing the detected lesion.

The ultrasound medical imaging apparatus 100 may transmit the ultrasound still image data to the external device 200.

The external device 200 may display an ultrasound streaming image 40h including at least one of the result 30h of detecting the lesion and the result of analyzing the detected lesion, based on the ultrasound streaming image data transmitted from the ultrasound medical imaging apparatus 100. Also, the external device 200 may display the ultrasound still image 50h including at least one of the result 30h of detecting the lesion and the result of analyzing the detected lesion, based on the ultrasound still image data.

Image quality of the ultrasound streaming image 40h may degrade according to the network environment of the communication network between the ultrasound medical imaging apparatus 100 and the external device 200. However, since the ultrasound still image 50h of high image quality is displayed, the doctor may identify the result value of measuring at least a part of the object.

Figure 13:
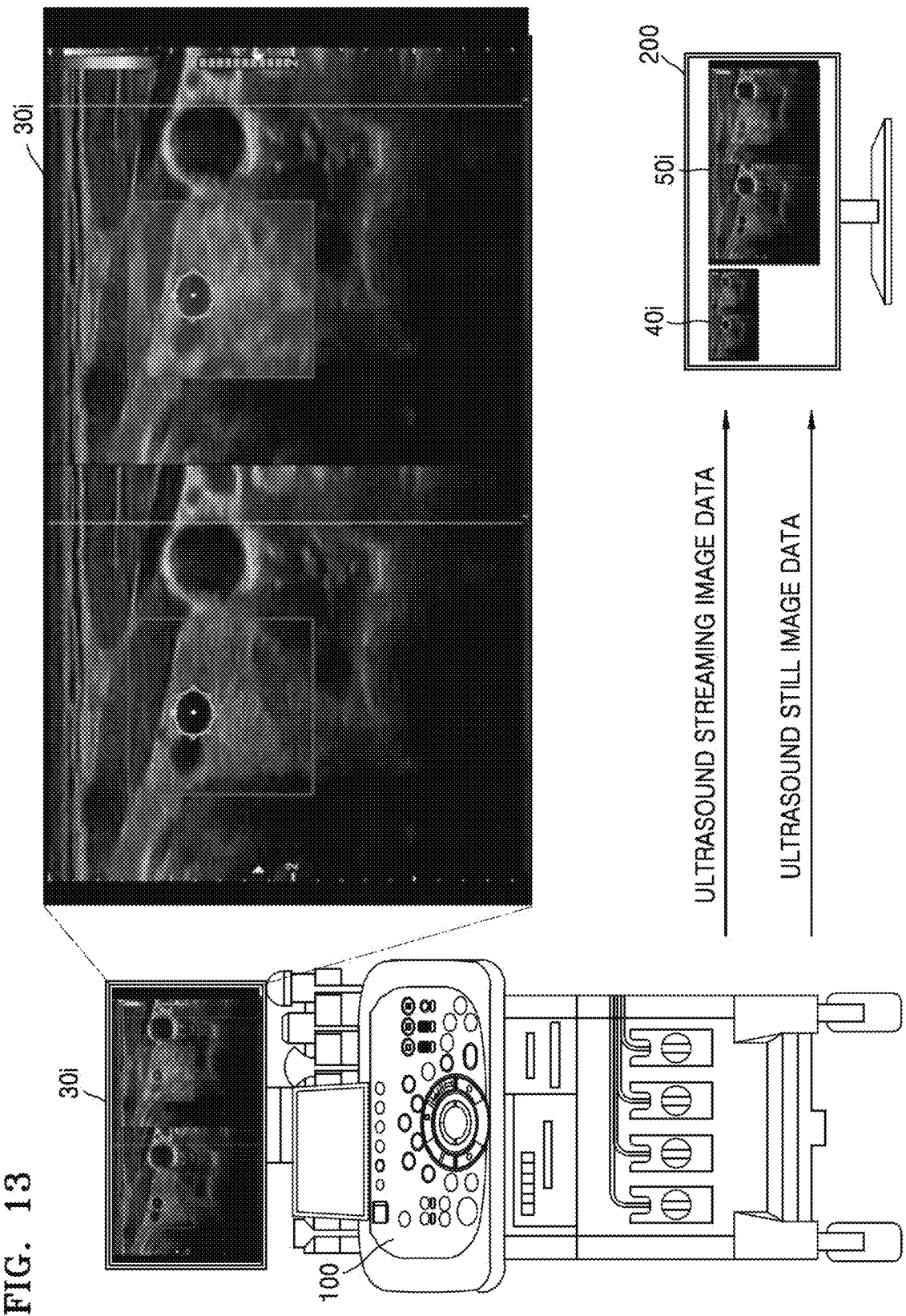
FIG. 13 is a diagram of an example of transmitting ultrasound streaming image data and ultrasound still image data, performed by an ultrasound medical imaging apparatus, to an external device, according to an embodiment.

FIG. 13 is a diagram of an example of transmitting ultrasound streaming image data and ultrasound still image data, performed by the ultrasound medical imaging apparatus 100, to an external device, according to an embodiment.

The ultrasound medical imaging apparatus 100 may display a result 30i of detecting a lesion from the ultrasound image of the object by using the CAD function. For example, as shown in FIG. 13, the ultrasound medical imaging apparatus 100 may display a result 30i of detecting a region that is suspected as a lesion from an ultrasound image of a thyroid. In detail, the ultrasound medical imaging apparatus 100 may display the result 30i of detecting the region suspected as a lesion by using contrast. The ultrasound medical imaging apparatus 100 may set the detected region as a region of interest.

The ultrasound medical imaging apparatus 100 may display a result of analyzing the detected lesion. Displaying of the result of analyzing the lesion is described above with reference to FIGS. 7, 8, and 11, and detailed descriptions of overlapping elements are omitted.

The ultrasound medical imaging apparatus 100 may generate ultrasound still image data including at least one of the result 30i of detecting the lesion by the CAD function and the result of analyzing the detected lesion.

The ultrasound medical imaging apparatus 100 may transmit the ultrasound still image data to the external device 200.

The external device 200 may display an ultrasound streaming image 40i including at least one of the result 30i of detecting the lesion and the result of analyzing the detected lesion, based on the ultrasound streaming image data transmitted from the ultrasound medical imaging apparatus 100. Also, the external device 200 may display an ultrasound still image 50i including at least one of the result 30i of detecting the lesion and the result of analyzing the detected lesion, based on the ultrasound still image data.

Image quality of the ultrasound streaming image 40i may degrade according to the network environment of the communication network between the ultrasound medical imaging apparatus 100 and the external device 200. However, since the ultrasound still image 50i of high image quality is displayed, the doctor may identify the result value of measuring at least a part of the object.

Figure 14:
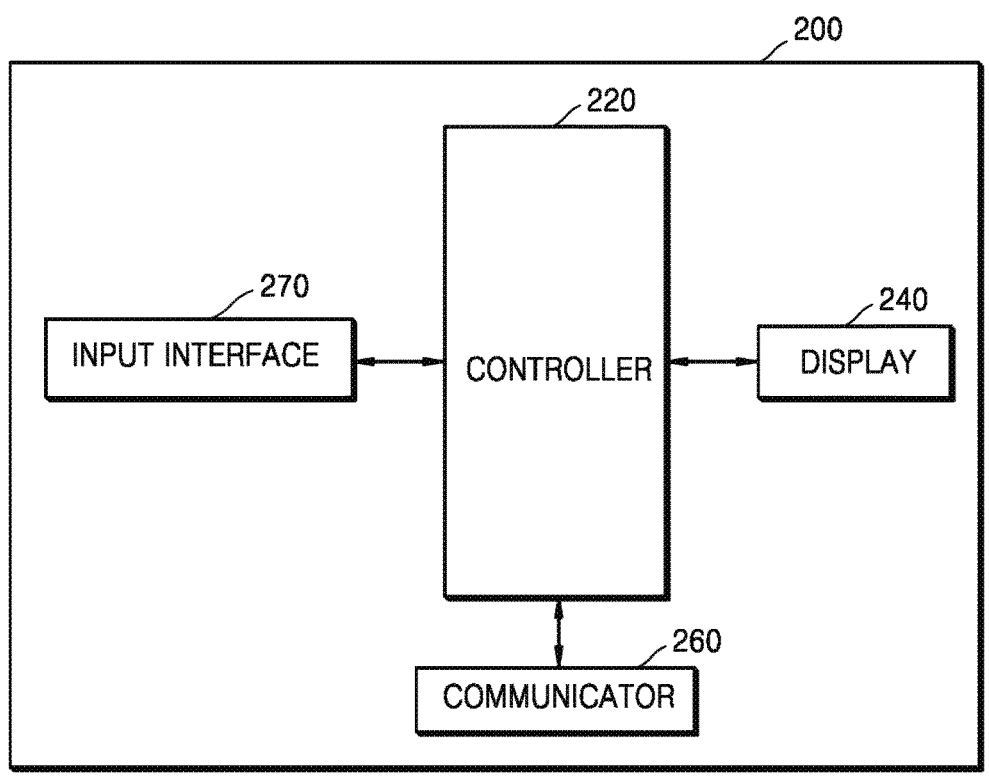
FIG. 14 is a block diagram of an external device that receives and displays ultrasound streaming image data and ultrasound still image data, according to an embodiment.
Figure 15:
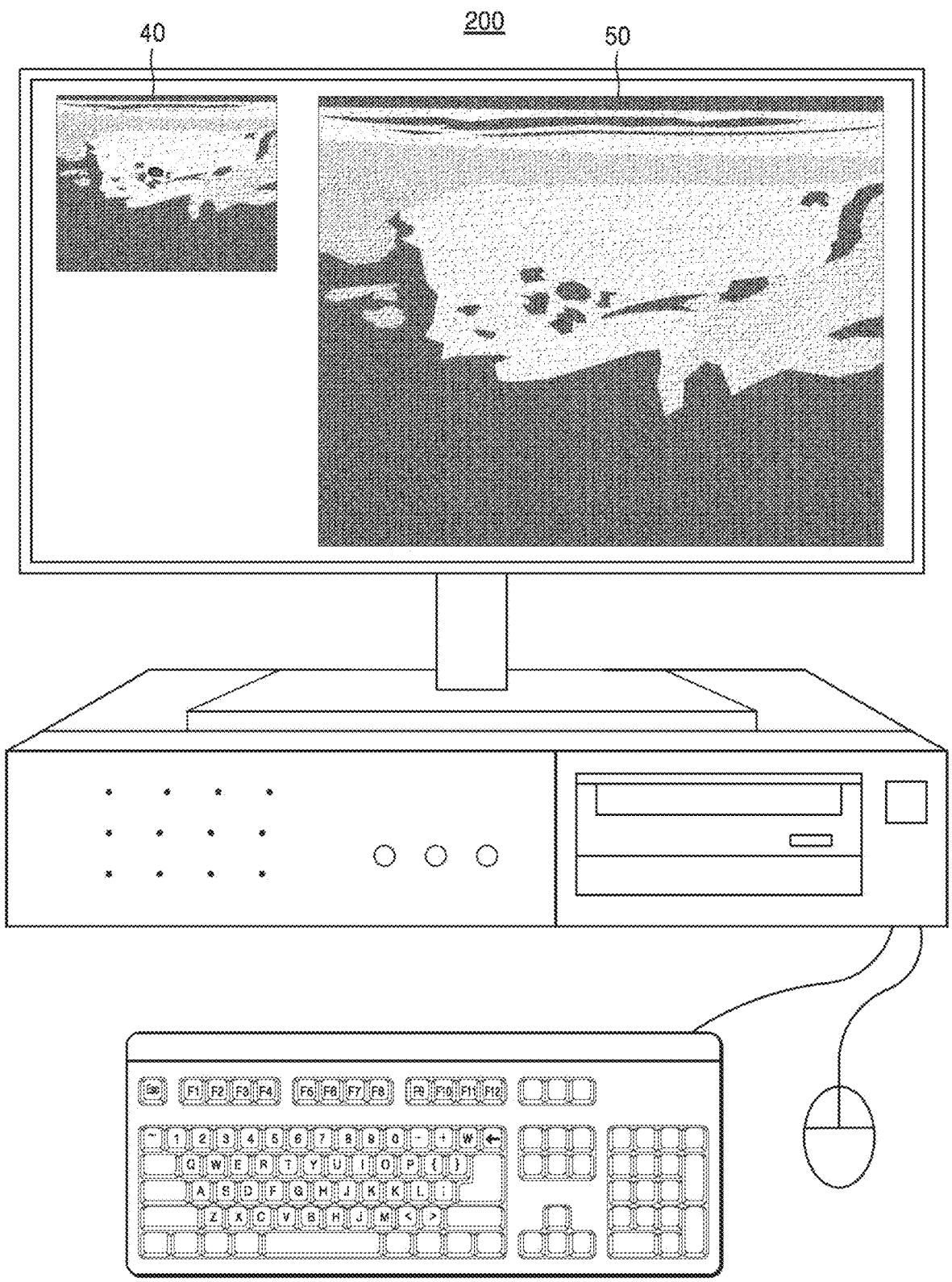
FIG. 15 is a diagram of an example of displaying an ultrasound streaming image and an ultrasound still image, by an external device, according to an embodiment.

FIG. 14 is a block diagram of the external device 200 that receives and displays ultrasound streaming image data and ultrasound still image data, according to an embodiment, and FIG. 15 is a diagram of an example of the external device 200 displaying the ultrasound streaming image and the ultrasound still image, according to an embodiment.

Referring to FIG. 14, the external device 200 may include a controller 220, a display 240, a communicator 260, and an input interface 270. However, not all the elements shown in FIG. 14 are essential elements of the external device 200. The external device 200 may include more or less elements than those of FIG. 14.

The controller 220 may include at least one processor. The controller 220 controls overall operations of the external device 200. For example, the controller 220 may generally control the input interface 270, the display 240, the communicator 260, etc. by executing programs stored in a memory (not shown). Also, the controller 220 may execute functions of the external device 200 illustrated with reference to FIGS. 3 to 13, by executing the programs stored in the memory (not shown).

According to an embodiment, the controller 220 may decode the ultrasound streaming image data transmitted from the ultrasound medical imaging apparatus 100 to display an ultrasound streaming image on the display 240.

According to an embodiment, the controller 220 may display an ultrasound still image on the display 240 by using ultrasound still image data transmitted from the ultrasound medical imaging apparatus 100.

According to an embodiment, the controller 220 may change a size of a region of displaying at least one of the ultrasound streaming image and the ultrasound still image, based on a user input.

According to an embodiment, the controller 220 may display an ultrasound still image selected based on the user input for selecting the ultrasound still image on the display 240.

According to an embodiment, the controller 220 may check the network environment between the ultrasound medical imaging apparatus 100 and the external device 200 (e.g., a bandwidth of the network, performance of the external device, capability, network speed, etc.) in real-time. The controller 220 may identify representations in the ultrasound medical imaging apparatus 100, based on received MPD. The controller 220 may select an appropriate representation based on the network environment, and control the communicator 260 to sequentially download fragments of the selected representation.

The display 240 may display information processed by the external device 200. Also, the display 240 may display an ultrasound streaming image 40 based on ultrasound streaming image data received by the external device 200 from the ultrasound medical imaging apparatus 100. The display 240 may display an ultrasound still image 50 based on ultrasound still image data received by the external device 200 from the ultrasound medical imaging apparatus 100.

The communicator 250 may generate a communication network with the ultrasound medical imaging apparatus 100. The communicator 250 may receive at least one of the ultrasound streaming image data and the ultrasound still image data from the ultrasound medical imaging apparatus 100.

The input interface 270 may receive a control signal from the user for displaying at least one of the ultrasound streaming image and the ultrasound still image.

The input interface 270 may receive a control signal from the user for changing a size of a region displaying at least one of the ultrasound streaming image and the ultrasound still image.

The input interface 270 may receive a control signal for selecting the ultrasound still image in order for the ultrasound still image selected by the user to be displayed on the display 240.

The above-described embodiments of the present inventive concept may be embodied in form of a computer-readable recording medium for storing computer executable instructions and data. The instructions may be stored in form of program codes and, when executed by a processor, may perform a certain operation by generating a certain program module. Also, when executed by a processor, the instructions may perform certain operations of the disclosed embodiments.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. An ultrasound medical imaging apparatus comprising:
an ultrasound probe configured to transmit an ultrasound signal to an object and receive an ultrasound echo signal from the object;
at least one processor configured to obtain ultrasound image data by using the ultrasound echo signal, generate ultrasound images based on the ultrasound image data, and generate an ultrasound streaming video based on the ultrasound images;
a display configured to display the ultrasound streaming video;
a user input interface configured to receive a control signal for setting calipers on the ultrasound streaming video; and
a communicator, wherein the at least one processor is further configured to:
control the communicator to transmit the ultrasound streaming video to an external device, and
in response to detecting a preset event while the communicator is transmitting the ultrasound streaming video to the external device, generate an ultrasound still image based on the ultrasound streaming video, control the communicator to stop transmitting the ultrasound streaming video to the external device, control the communicator to transmit the ultrasound still image to the external device while controlling the communicator to stop transmitting the ultrasound streaming video, and control the communicator to transmit the ultrasound streaming video after being done with transmitting the ultrasound still image to the external device,
wherein the preset event comprises receiving of the control signal for setting calipers on the ultrasound streaming video.

2. The ultrasound medical imaging apparatus of claim 1, wherein the second data is data of an image having a higher resolution than a resolution of a frame included in the first data.

3. The ultrasound medical imaging apparatus of claim 1, wherein the communicator is further configured to transmit the second data and the first data to the external device by respectively using separate communication ports.

4. The ultrasound medical imaging apparatus of claim 3, wherein the communicator is further configured to transmit the second data to the external device in priority over first data, based on a bandwidth and transmission speed of a communication network formed between the ultrasound medical imaging apparatus and the external device.

5. The ultrasound medical imaging apparatus of claim 1, wherein the user input interface is further configured to receive a control signal for freezing the ultrasound streaming video, and the preset event further comprises receiving of the control signal for freezing the ultrasound streaming video.

6. The ultrasound medical imaging apparatus of claim 1, wherein the user input interface is further configured to receive a control signal for measuring a size of at least a part of the object included in the ultrasound streaming video, and
wherein the preset event further comprises receiving of the control signal for measuring the size of at least the part of the object, and
wherein the ultrasound still image further comprises a measuring result value.

7. The ultrasound medical imaging apparatus of claim 1, wherein the display is further configured to display a result report including a result value of measuring at least a part of the object,
wherein the preset event further comprises displaying of the result report, and
wherein the ultrasound still image further comprises the result report.

8. The ultrasound medical imaging apparatus of claim 1, wherein the communicator is further configured to transmit at least one of the ultrasound image data and a result report including a result value of measuring at least a part of the object, to a server connected through a picture archiving and communication system (PACS), and the preset event further comprises transmitting of the ultrasound image data and the result report including the result value of measuring at least the part of the object to the server connected through the PACS, wherein the ultrasound still image further comprises the result report.

9. The ultrasound medical imaging apparatus of claim 1, wherein the preset event further comprises detecting of the ultrasound probe moving a predetermined reference number of times or less per unit time.

10. A method of controlling an ultrasound medical imaging apparatus, the method comprising:
transmitting, by an ultrasound probe, an ultrasound signal to an object and receiving an ultrasound echo signal from the object;
obtaining ultrasound image data by using the ultrasound echo signal;
generating ultrasound streaming video based on the ultrasound image data;
displaying the ultrasound streaming video;
receiving a control signal for setting calipers on the ultrasound streaming video;
transmitting the ultrasound streaming video to an external device; and
in response to detecting a preset event while transmitting the ultrasound streaming video to the external device, generating an ultrasound still image based on the ultrasound streaming video, stopping transmission of the ultrasound streaming video to the external device, transmitting the ultrasound still image to the external device while stopping transmission of the ultrasound streaming video to the external device, and transmitting the ultrasound streaming video after being done with transmitting the ultrasound still image to the external device,
wherein the preset event comprises receiving of the control signal for setting calipers on the ultrasound streaming video.

11. The method of claim 10, wherein the second data is data of an image having a higher resolution than a resolution of a frame included in the first data.

12. The method of claim 10, wherein the second data and the first data are respectively transmitted to the external device by using separate communication ports.

13. The method of claim 12, wherein the second data is transmitted to the external device in priority over the first data, based on a bandwidth and transmission speed of a communication network formed between the ultrasound medical imaging apparatus and the external device.

14. The method of claim 10, further comprising receiving a control signal for obtaining an ultrasound image of the object, wherein the preset event further comprises receiving of the control signal for freezing the ultrasound streaming video.

15. The method of claim 10, further comprising receiving a control signal for measuring a size of at least a part of the object included in the ultrasound streaming video, wherein the preset event further comprises receiving of the control signal for measuring the size of at least the part of the object, wherein the ultrasound still image further comprises a measuring result value.

16. The method of claim 10, further comprising:
displaying a result report including a result value of measuring at least a part of the object,
wherein the preset event further comprises displaying of the result report, wherein the ultrasound still image further comprises the result report.

17. The method of claim 10, further comprising:
transmitting at least one of the ultrasound image data and a result report including a result value of measuring at least a part of the object, to a server connected through a picture archiving and communication system (PACS), wherein the preset event further comprises transmitting of the ultrasound image data and the result report including the result value of measuring at least a part of the object to the server connected through the PACS, wherein the ultrasound still image further comprises the result report.

18. The method of claim 10,
wherein the preset event further comprises detecting of the ultrasound probe moving a predetermined reference number of times or less per unit time.

* * * * *